(12) United States Patent
Lepore

(10) Patent No.: US 8,822,707 B2
(45) Date of Patent: Sep. 2, 2014

(54) NUCLEOPHILE ASSISTING LEAVING GROUPS

(75) Inventor: Salvatore Lepore, Delray Beach, FL (US)

(73) Assignee: Florida Atlantic University, Boca Raton, FL (US)

( * ) Notice: Subject to any disclaimer, the term of this patent is extended or adjusted under 35 U.S.C. 154(b) by 883 days.

(21) Appl. No.: 11/667,414

(22) PCT Filed: Nov. 14, 2005

(86) PCT No.: PCT/US2005/041019
§ 371 (c)(1),
(2), (4) Date: Dec. 3, 2007

(87) PCT Pub. No.: WO2006/060142
PCT Pub. Date: Jun. 8, 2006

(65) Prior Publication Data
US 2008/0221347 A1    Sep. 11, 2008

Related U.S. Application Data

(60) Provisional application No. 60/629,071, filed on Nov. 18, 2004.

(51) Int. Cl.
*C07C 309/77* (2006.01)
*C07C 309/89* (2006.01)
*C07D 323/00* (2006.01)
*C07H 11/00* (2006.01)

(52) U.S. Cl.
CPC .............. *C07H 11/00* (2013.01); *C07C 309/89* (2013.01); *C07C 309/77* (2013.01); *C07C 2103/74* (2013.01); *C07D 323/00* (2013.01)
USPC .............................. 549/352; 549/353; 560/11

(58) Field of Classification Search
None
See application file for complete search history.

(56) References Cited

U.S. PATENT DOCUMENTS

| | | | | |
|---|---|---|---|---|
| 5,459,026 A | * | 10/1995 | Nakamura et al. | 430/587 |
| 6,015,909 A | * | 1/2000 | Fujiwara et al. | 548/243 |
| 2003/0207774 A1 | * | 11/2003 | Negoro et al. | 508/258 |

FOREIGN PATENT DOCUMENTS

JP          04022945   *   1/1992   ............. G03C 7/36

OTHER PUBLICATIONS

Lepore et al. Arylsulfonate-Based Nucleophile Assisting Leaving Groups. J. Org. Chem. 2005, 70, pp. 8117-8121.*
Shikhiev et al. Sin. Prevrashch. Monomernykh Soedin. (1967), 179-82.*
CAPlus record, Accession No. 1969:11032. Obtained from STN search, accessed Aug. 4, 2009.*
CAPlus search via STN. Answer 15 of 33. Sepplemental to JP 04022945 above. See structure, bottom p. 1. (1992).*
International Search Report for related PCT Application No. PCT/US2005/041019, dated Sep. 29, 2006, 2 pages.
Written Opinion for related PCT Application No. PCT/US2005/041019, dated Sep. 29, 2006, 7 pages.
Roberts, John D., et al., Basic Principles of Organic Chemistry, W.A. Benjamin, Inc., New York, New York, (1964), p. 762.
Zehavi, J. Org. Chem., 40, 3870 (1975).
Wu et al., J. Org. Chem., 39, 3014 (1974).
Wang et al, J. Org. Chem., 55, 2344 (1990).
Pedersen, J. Am. Chem. Soc., 89, 7017 (1967).
Pedersen, et al., Angew. Chem. Int. Ed., 11, 16 (1972).
Stott, et al., J. Am. Chem. Soc., 102, 4810 (1980).
Kimura, et al. J. Org. Chem., 47, 2493 (1982).
Kimura, et al., J. Org. Chem., 48, 195 (1983).
Solov'ev, et al., J. Chem. Soc., Perkin Trans. 2., 1489 (1998).
Gobbi, et al., J. Org. Chem. 60, 5954 (1995).
Lippard, C & E News, Aug. 7, p. 64 (2000).
Loev, et al., J. Org. Chem., 27, 1703 (1962).
Choudhary, et al., Tetrahedron, 56, 7291 (2000).
Mizutani, et al., J. Org. Chem., 65, 6097 (2000).
Maitra, Tetrahedron Lett., 39, 3255 (1998).
Solov'ev, et al., J. Org. Chem., 61, 5221 (1996).
Adrian, et al., J. Am. Chem. Soc., 113, 678 (1991).
Dishong, et al., J. Org. Chem., 47, 147 (1982).
Suenaga, et al., Tetrahedron Lett., 44, 5799 (2003).
Pankova, et al., Z. Coll. Czech. Chem. Commun., 45, 3150 (1980).
Lepore, et al., Angew. Chem. Int. Ed. 47, 7511-7514 (2008).
Lu, et al., J. Org. Chem., 74, 5290-5296 (2009).
Braddock, et al., 2009 (not yet assigned a volume and page number)
Park, et al., Angew. Chem. Int. Ed. 46, 4726-4728 (2007).

* cited by examiner

*Primary Examiner* — Alicia L Otton
(74) *Attorney, Agent, or Firm* — Saliwanchik, Lloyd & Eisenschenk

(57) ABSTRACT

Sulfonate leaving groups include a cation chelating moiety, e.g. a polyether or crown ether. The chelating moiety stabilizes the sulfonate leaving group by forming a complex with a cation of a cation-nucleophile combination. The stabilized leaving group is more easily displaced under many conditions than are standard arylsulfonate leaving groups such as the tosyl group. The chelating moiety also favors certain cations depending on the identity of the moiety thereby enhancing the reaction rate with nucleophilic salts containing the preferred cation. Use of the inventive leaving groups results in improved yields, decreased reaction times and improved product purity.

13 Claims, 11 Drawing Sheets

NUCLEOPHILE ASSISTING LEAVING GROUPS

RELATED APPLICATIONS

This application claims priority to U.S. Ser. No. 60/629,071, filed on Nov. 18, 2004, and is herein incorporated by reference in its entirety.

STATEMENT OF GOVERNMENT INTEREST

This invention was made with government support under grant number R03 MH66963-01 awarded by the National Institute of Mental Health, a component of the National Institutes of Health. The United States government has certain rights in the invention.

FIELD OF THE INVENTION

The present invention provides reagents and starting materials for use in nucleophilic substitution reaction. The invention further provides methods of making compounds using such reagents and starting materials.

BACKGROUND OF THE INVENTION

The $S_N2$ reaction mechanism is well known in the art. The shorthand $S_N2$ means substitutions nucleophilic, bimolecular, which indicates that a nucleophile (Nuc) displaces a leaving group (LG) at a tetrahedral carbon center leading to an inversion of stereochemistry (Walden inversion). The general scheme can be depicted as follows:

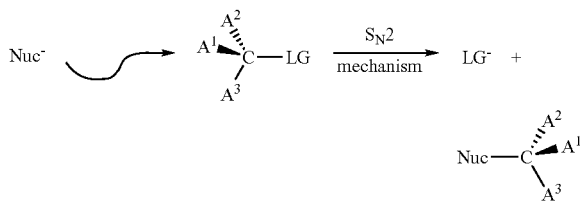

The $S_N2$ reaction is ubiquitous in the art due to its general utility. Many substituents on commonly synthesized compounds, including pharmaceuticals, diagnostic compounds, fungicides, bacteriocides, virucides, etc. possess one or more function groups that can be envisioned as nucleophiles in the $S_N2$ reaction.

Exemplary nucleophiles that are known in the art include halides (e.g. F, Cl, Br and I), cyanide (CN), azide ($N_3$), nitride, etc. While many compounds having such groups are known, it is often the case that starting materials having easily displaceable leaving groups are hard to come by.

One class of starting materials that is difficult to substitute with a nucleophile, but which would be expected to provide a rich source of starting materials, includes alcohols. Alcohols are ubiquitous in nature. From methanol and ethanol, which are commonly produced by fermentation of sugars to sugars themselves (both simple and complex), there is a wide variety of alcohols that could be converted to their corresponding halides, azides, nitrides and cyanides. However, it has been difficult to convert alcohols to halides, azides and cyanides (amongst others), by the $S_N2$ pathway, as the OH group of alcohols is a strong base and thus a poor leaving group for nucleophilic substitution.

It is known to prepare aryl sulfonates of hydroxyl-bearing compounds and aryl sulfonate esters of benzene sulfonic acids (such as tosylates) have been used with great advantage to make a variety of compounds wherein the hydroxyl groups are displaced by nucleophiles, such as halides, azides and cyanides. However, there are still situations in which the reaction kinetics are unfavorable for using such reagents to prepare compounds in which an alcohol has been replaced by a nucleophile. Furthermore, nucleophiles often react with substrates containing an leaving group in unintended ways leading to unwanted side products.

There is a need for leaving groups that can be displaced by nucleophiles in high yields and in a timely fashion.

There is a need for leaving groups that are selective for a given cation of a nucleophilic salt thereby promoting an $S_N2$ reaction involving the nucleophilic salt to occur at the intended site on the substrate.

There is a need for selective and rapid-reacting leaving groups that are attached to an insoluble support to allow for the facilitate separation of the these leaving groups from the desired products by filtration There is a further need for reagents that can be used to synthesize such leaving groups.

There is a further need for methods of using said reagents to prepare chemical entities containing such leaving groups.

There is further a need for methods of making target compounds containing a desired nucleophile as part of its structure from starting materials, wherein the starting materials have leaving groups that are easily displaced by $S_N2$-type reaction.

These and other needs are met by embodiments of the present invention.

SUMMARY OF THE INVENTION

The invention meets the foregoing needs by providing novel leaving groups for use in $S_N2$-type reactions. The inventive leaving groups include aryl sulfonate and other sulfonate leaving groups that include a metal chelating group. The metal chelating group stabilizes the transition complex, thereby lowering the kinetic energy barrier to the $S_N2$ reaction, whereby the rate of the chemical reaction, as well as (in some cases at least) its specificity, are greatly enhanced.

The invention also provides starting materials, intermediates and methods of using the novel leaving groups.

Other uses and advantages will be apparent to the person of skill in the art upon review of the following description, claims and figures.

DETAILED DESCRIPTION OF THE INVENTION

Figure 1:
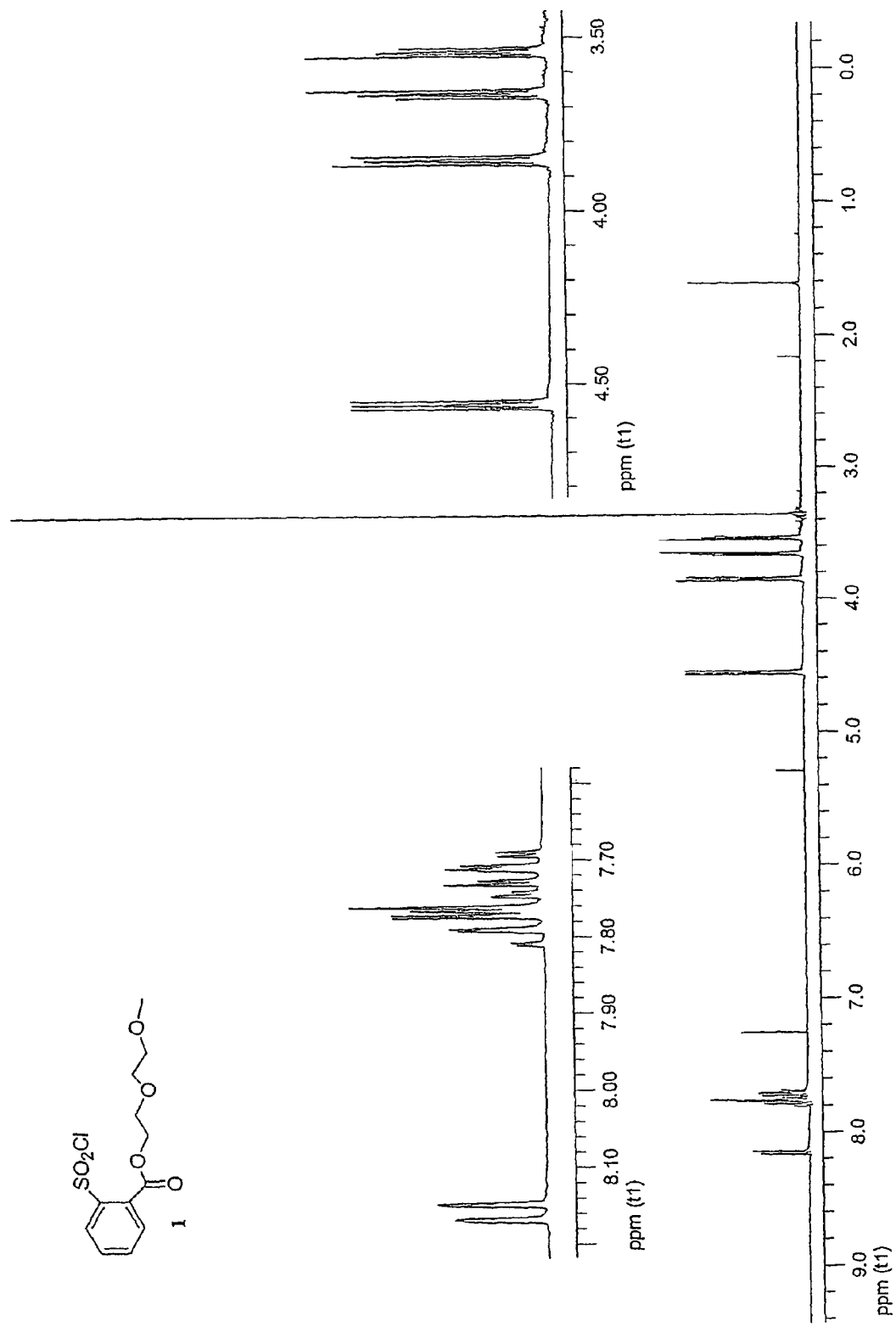
FIGS. 1-11 provide structures and NMR spectra for various compounds according to the invention.
Figure 2:
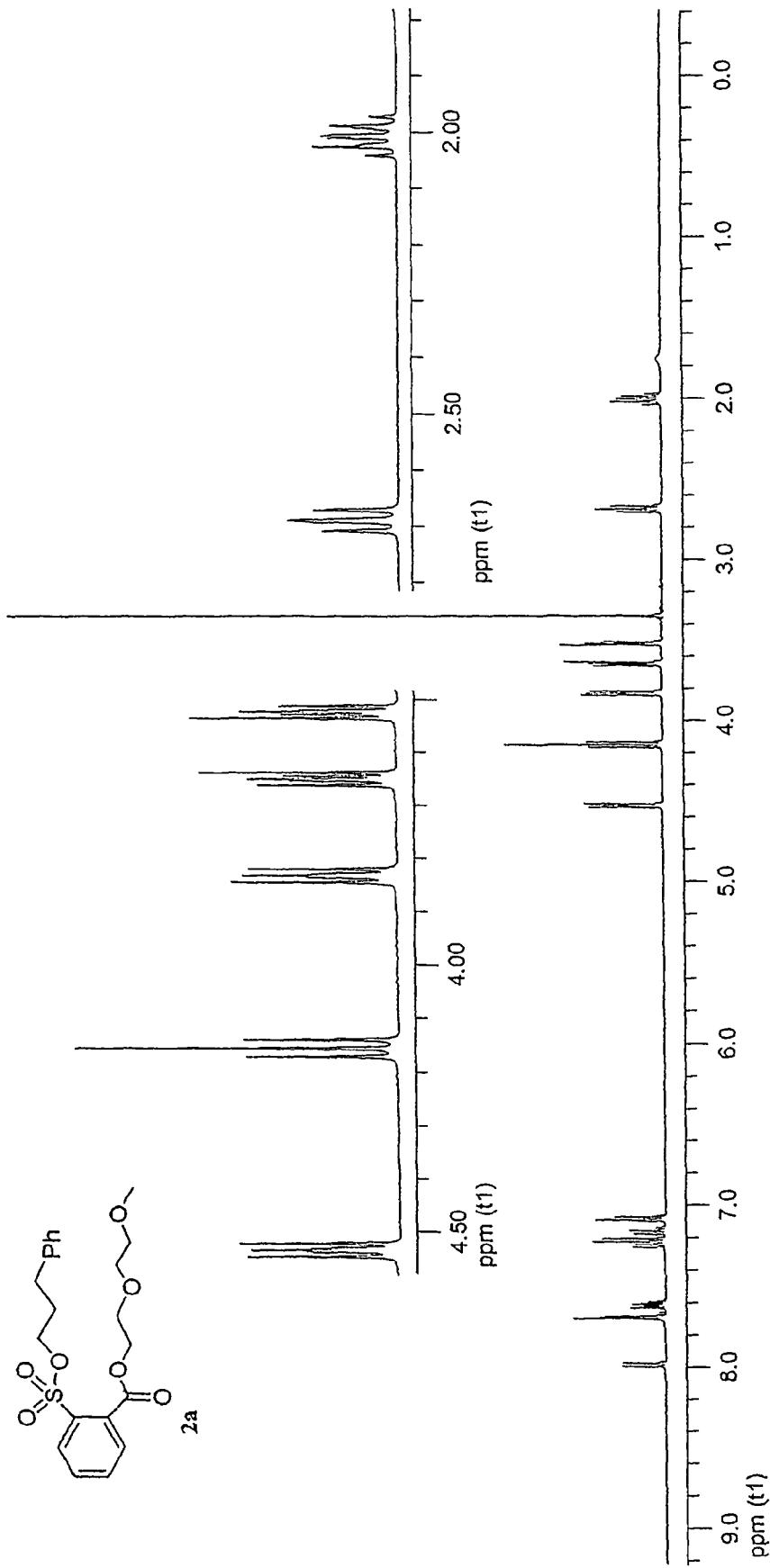
Figure 3:
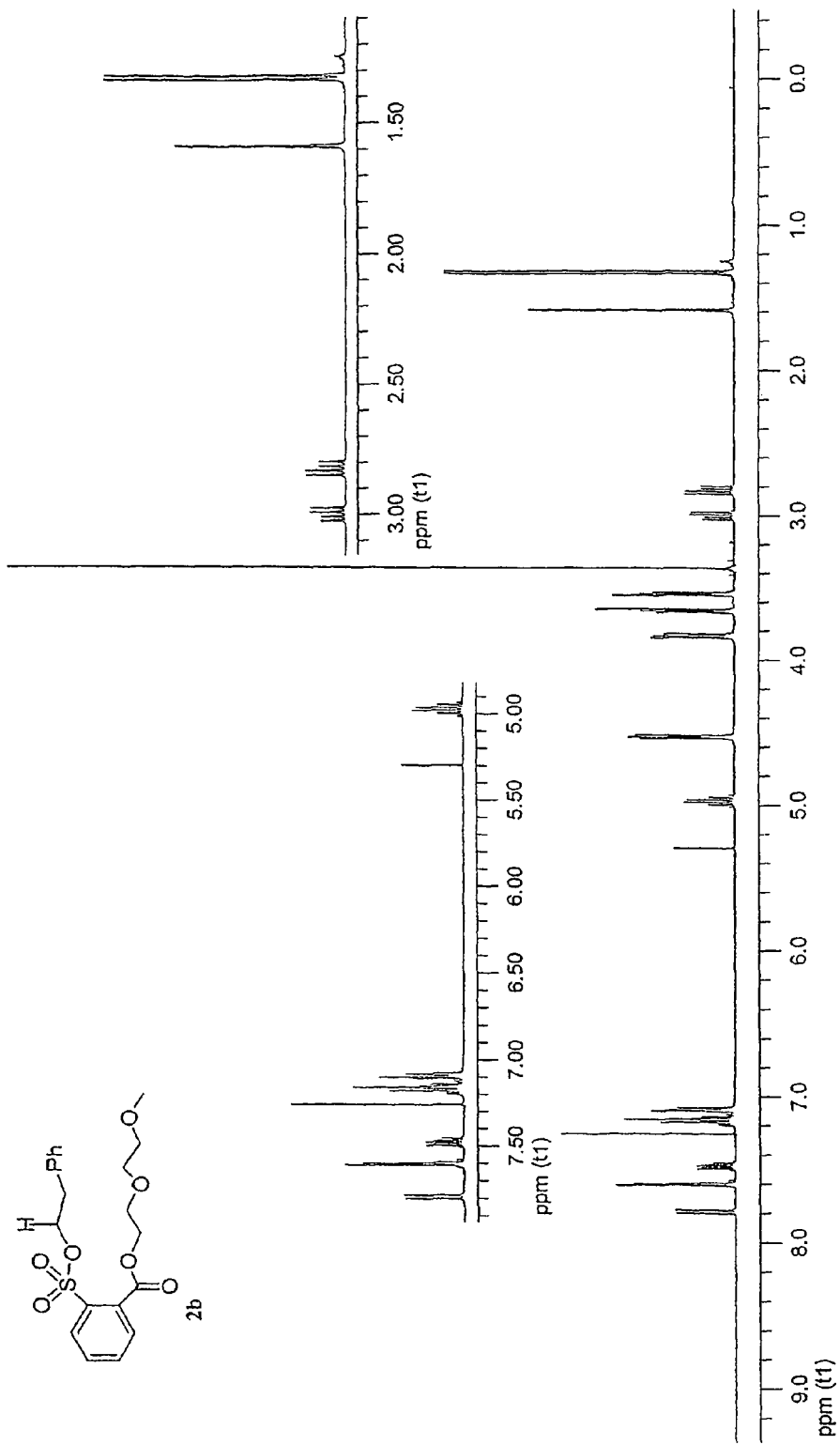
Figure 4:
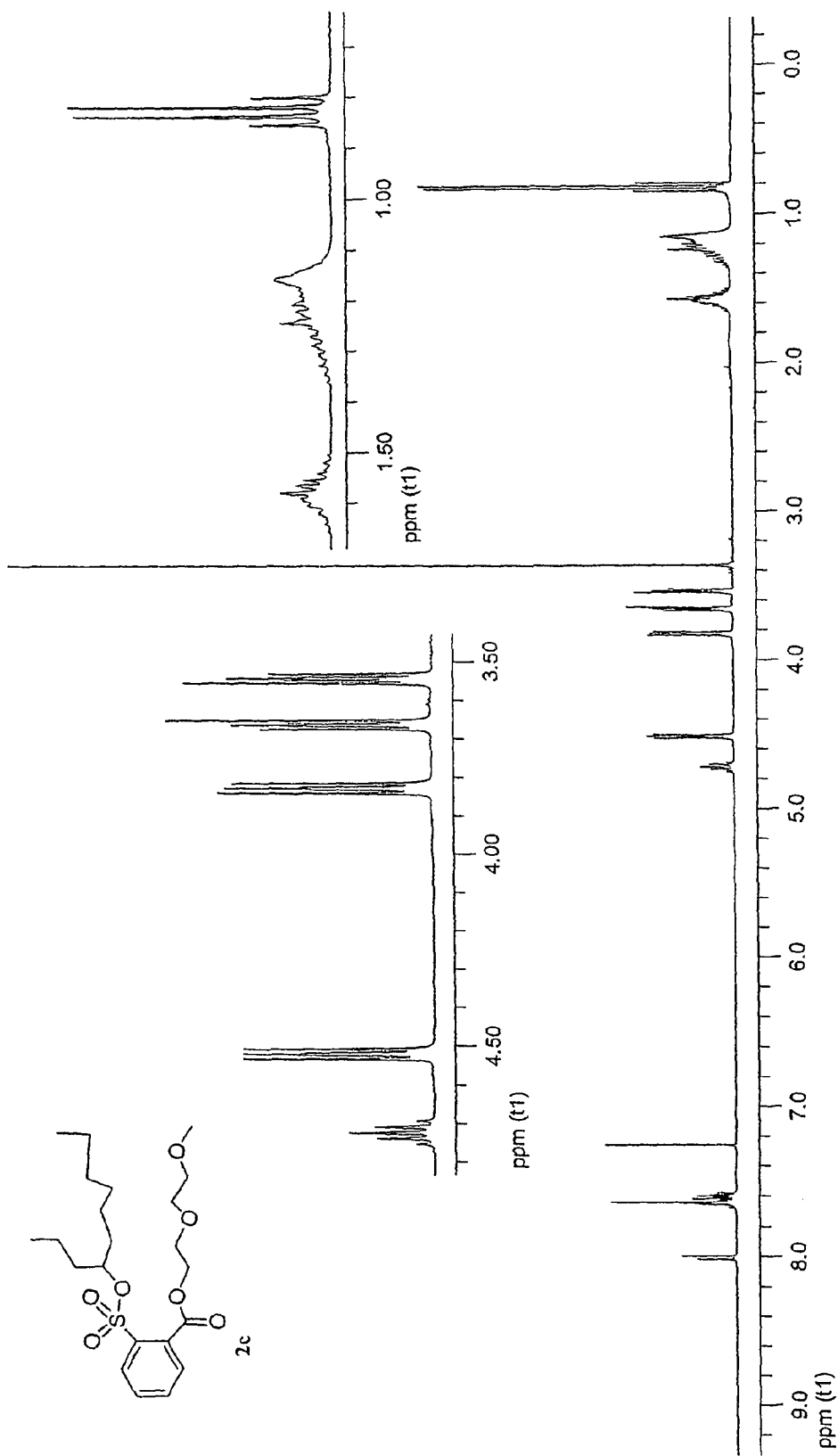
Figure 5:
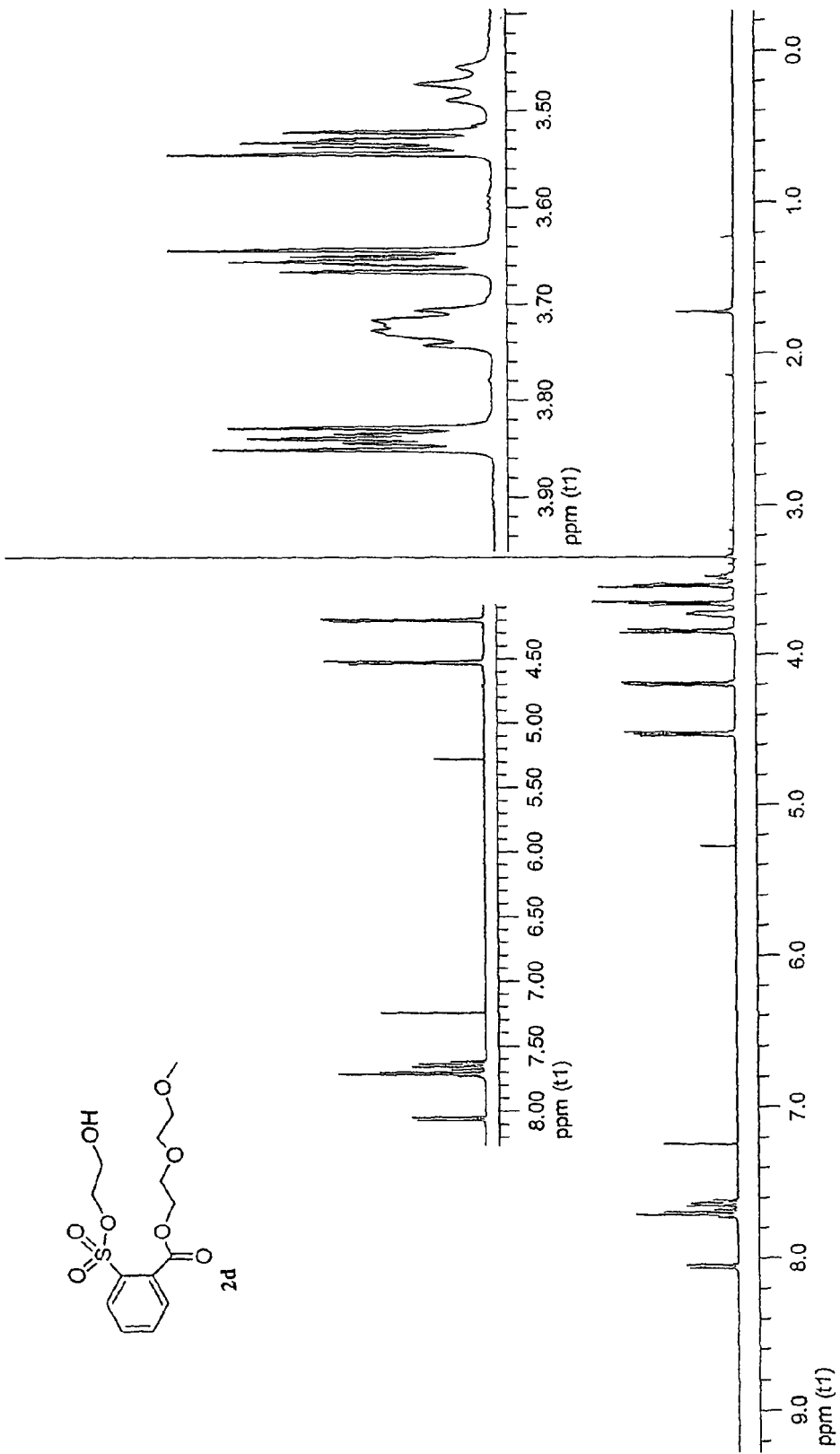
Figure 6:
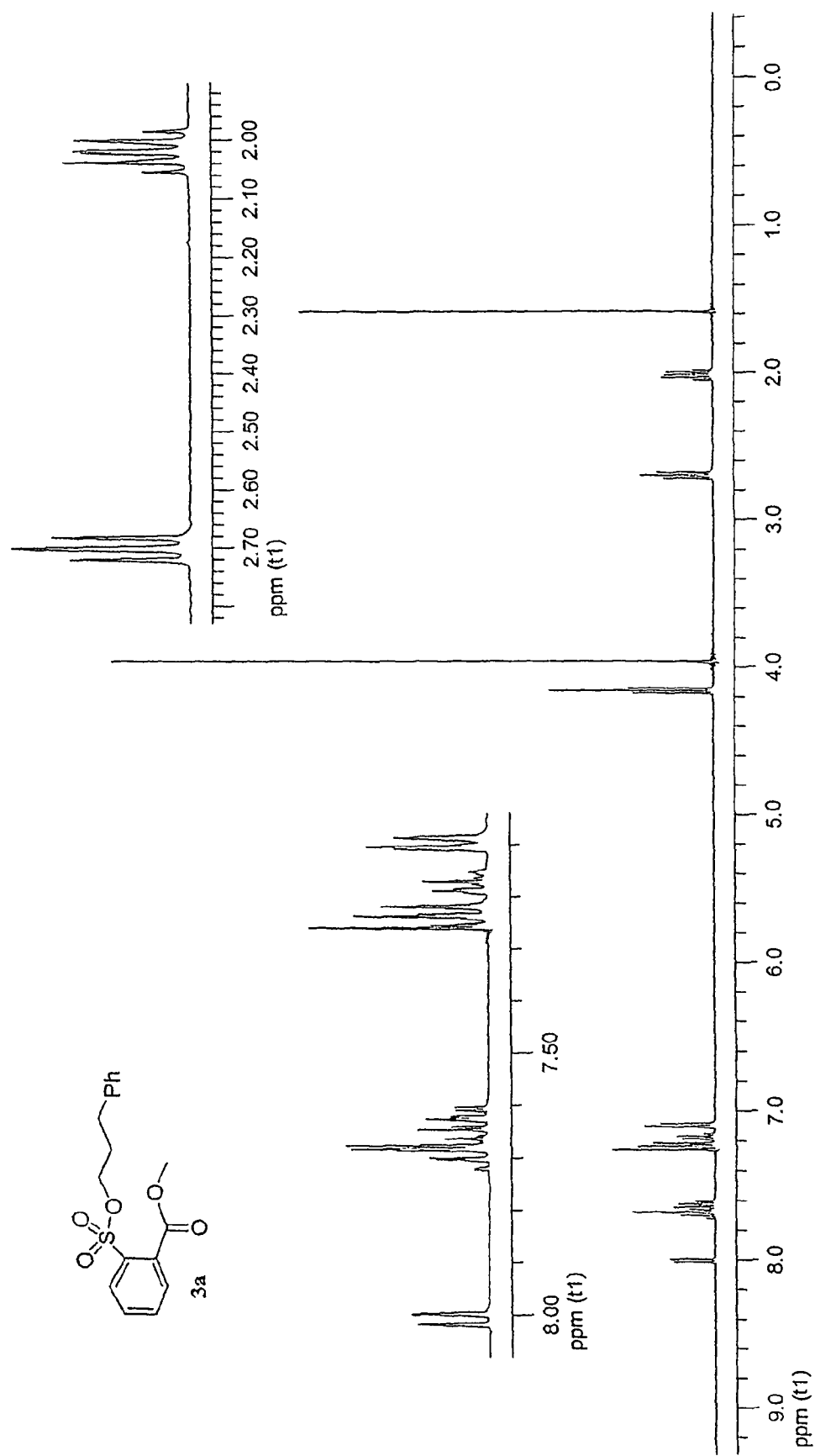
Figure 7:
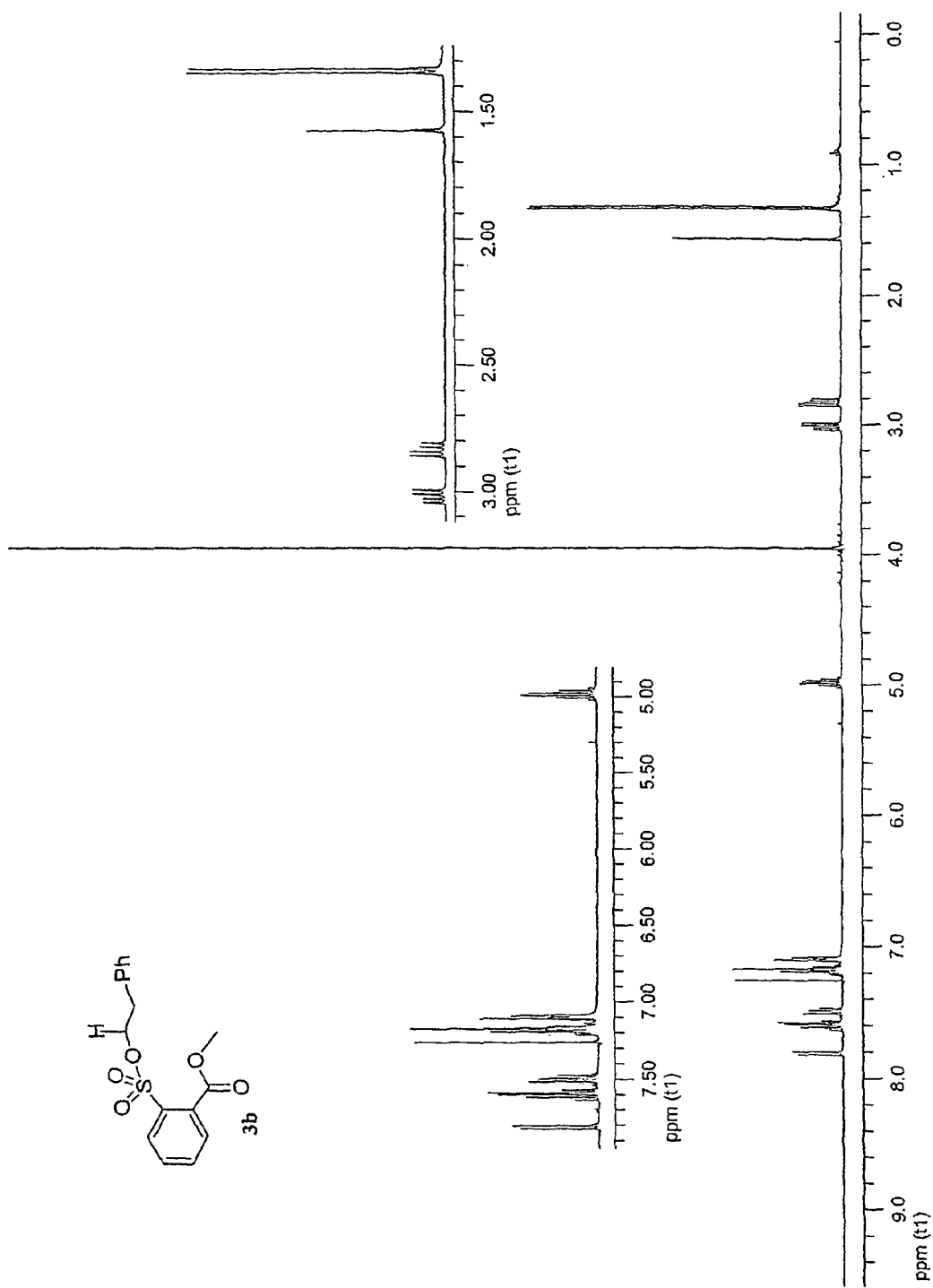
Figure 8:
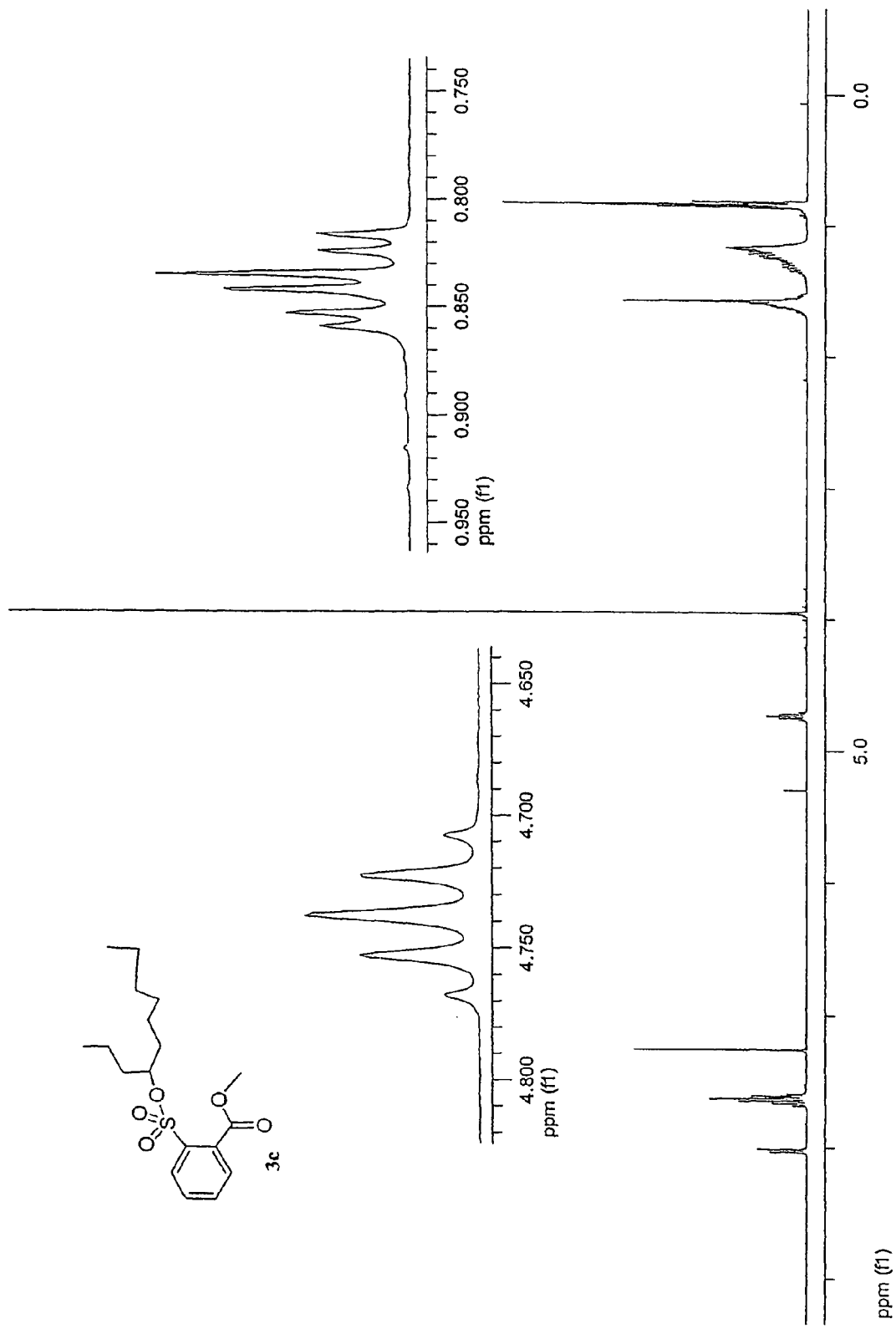
Figure 9:
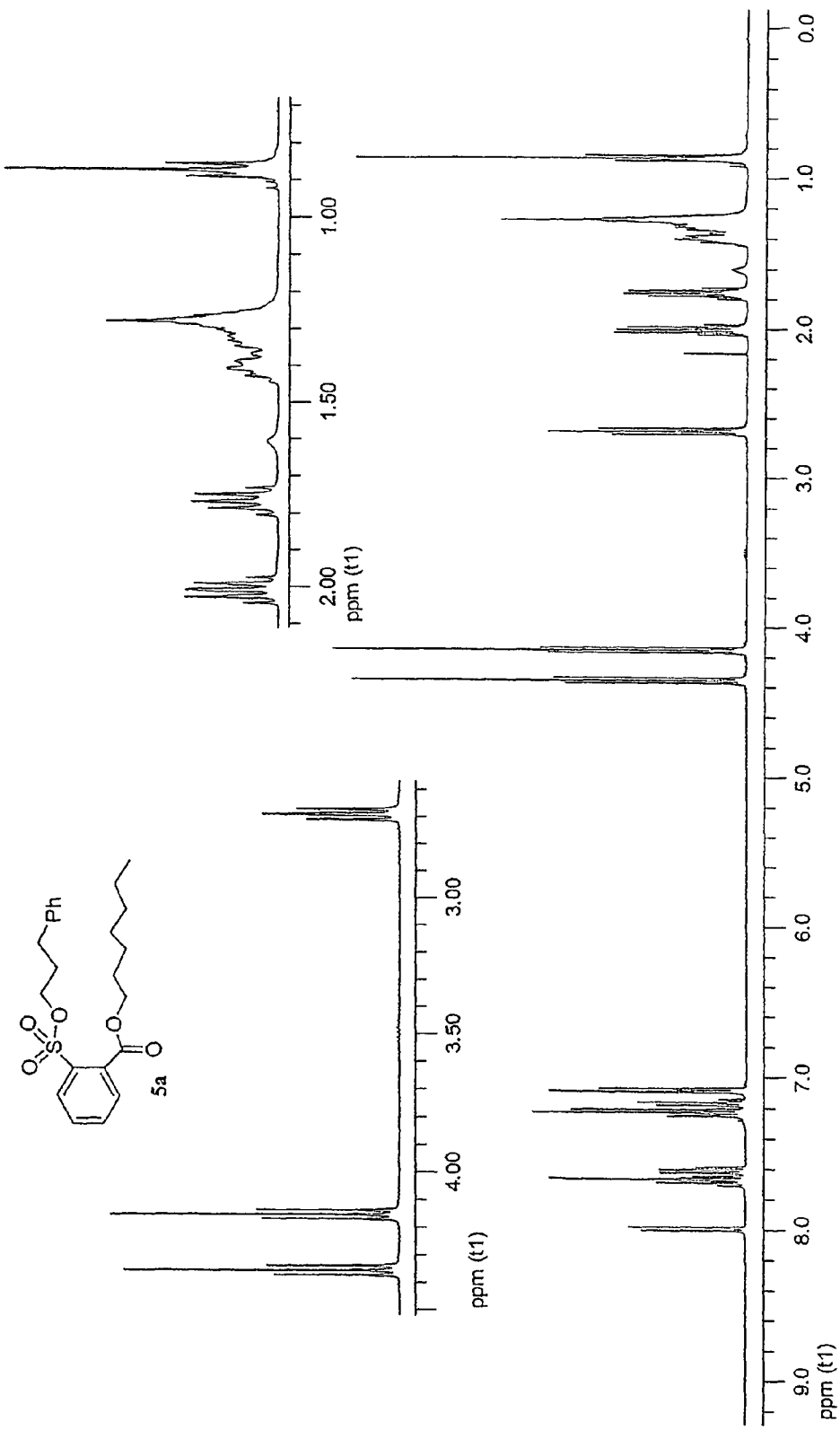
Figure 10:
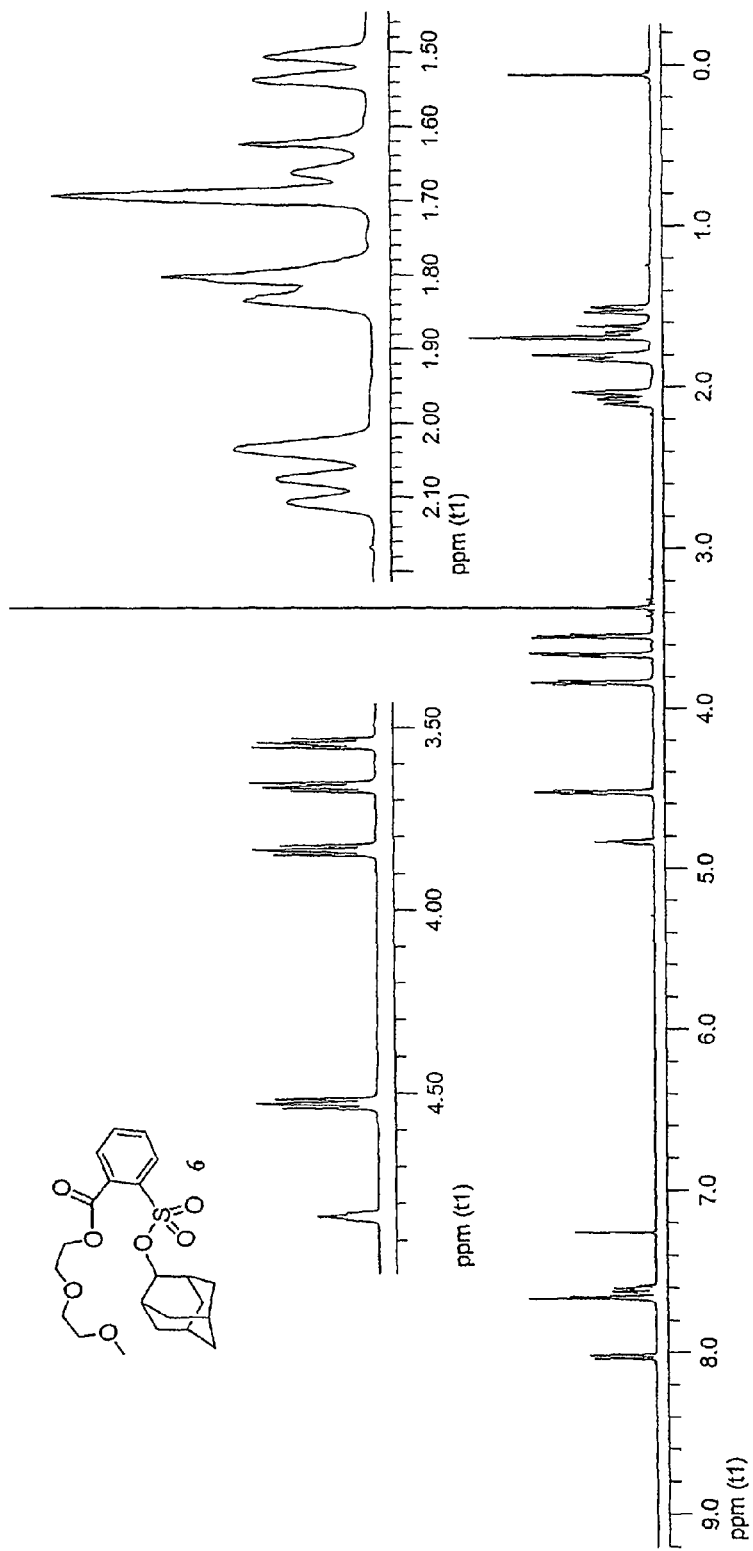
Figure 11:
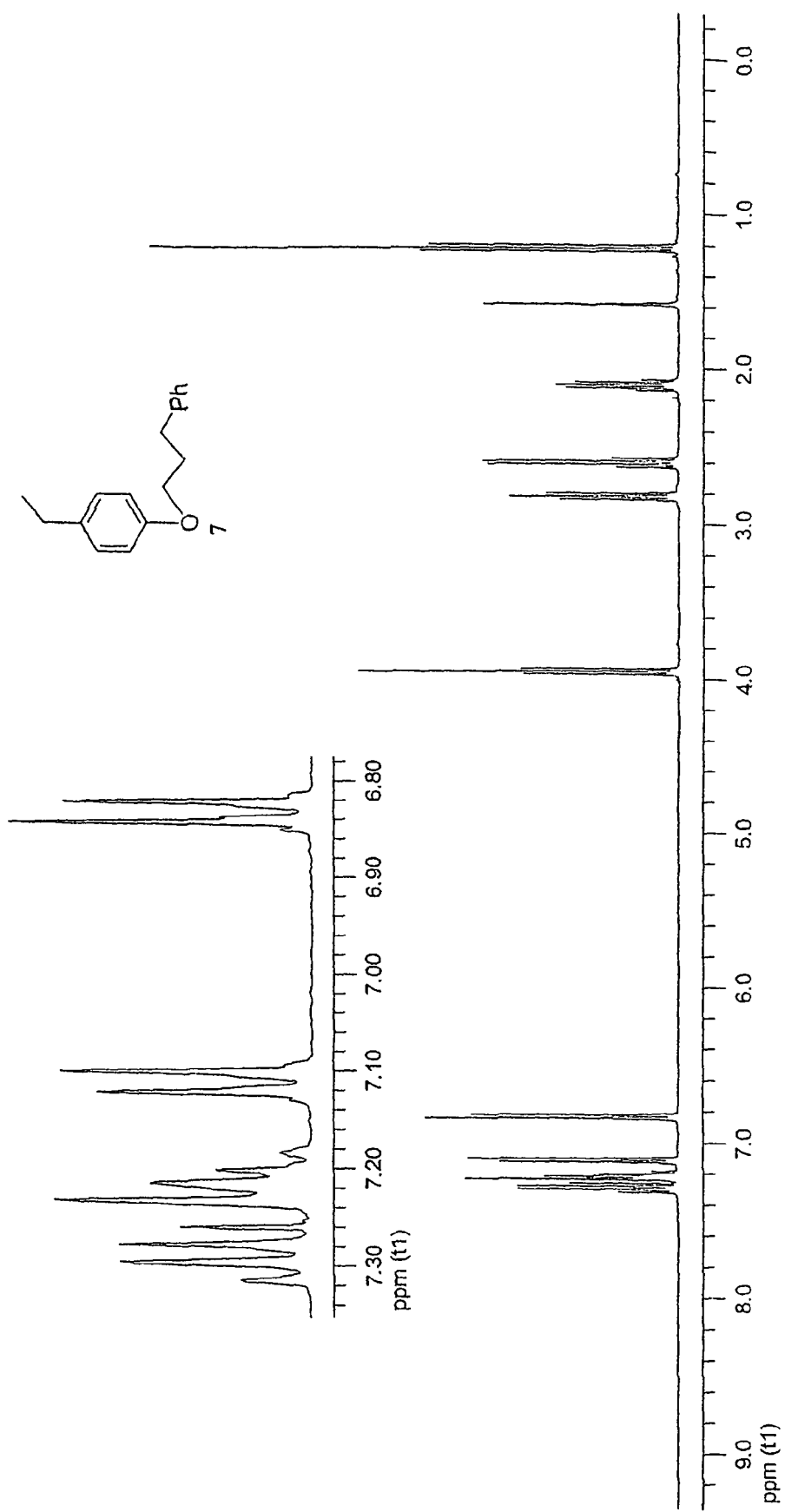

The invention provides reagents of the general formula:

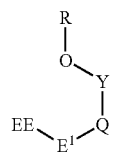

wherein:
- EE is a cation-chelating moiety such as a polyether or a crown ether. The various oxygens of the ether group may also be replaced by nitrogen, sulfur, and phosphorous atoms
- $E^1$ is a direct bond or a linking group
- Q is an acyclic or cyclic group (including heterocyclic, aromatic, or heteroaromatic)
- Y is $SO_2$ or $SiR^6R^7$, wherein each of $R^6$ and $R^7$ is independently an acyclic or cyclic group (including heterocyclic, aromatic, or heteroaromatic)
- R is an optionally substituted allyl group (including cyclic and heterocyclic), an optionally substituted alkenyl group, an optionally substituted alkynyl group or an optionally substituted aromatic or heteroaromatic group
- EE, $E^1$, Q, and $R^6$ & $R^7$ (when Y=Si) may be covalently linked to an insoluble polymer or silica gel resin for use in solid-phase synthesis applications A surprising rate enhancement in the nucleophilic substitution reaction takes place to give product R-Nuc and a leaving group has been observed when a substrate of the foregoing formula is reacted with a compound of the formula $M^{x+}Nuc^-_x$ (or $M^{x+}Nuc^{x-}$), wherein M is a cation, x is the charge of the cation and Nuc is a nucleophile. The reaction can be summarized as in the following scheme:

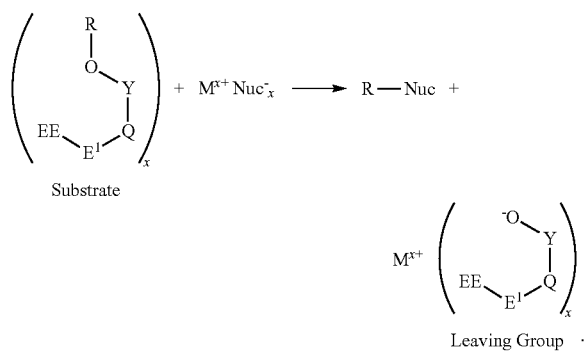

In some embodiments, x is 1, 2 or 3. In particular embodiments, x is 1. In some specific embodiments, $M^{x+}$ is $Li^+$, $Na^+$, or $K^+$.

As disclosed above, Nuc is a functional group which functions as a nucleophile in the foregoing reaction. Nuc may be a nucleophile known in the art, such as a halide (F, Cl, Br, I), CN, SCN, NCS, $N_3$, $^-OR'$ (wherein R' is the same as or different from R), $^-SR''$ (wherein R'' is the same as or different from R), etc. Both R' and R'' may be an optionally substituted allyl group or a cyclic group (including heterocyclic, aromatic, or heteroaromatic). In particular embodiments, Nuc may be an isotopically enriched nucleophile, such as $^{18}F$, radioactive iodine, C-isotopes of cyanide ($^{11}C$, $^{13}C$, or $^{14}C$), etc.

While not wishing to be bound by theory, it is believed that the increased reaction rate achieved in the foregoing reaction scheme is due to two reasons:

1) The formation of a complex in which the forming negative charge on the oxygen of the leaving group is stabilized by the cation ($M^{x+}$) which is held nearby the oxygen by the EE variable group thereby lowering the enthalpic barrier to the reaction. Such a stabilized complex can be envisioned as follows:

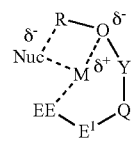

2) The Nuc of the $M^{x+}Nuc^-_x$ reagent is brought closer to R by interaction of the $M_{x+}$ with EE which is nearby R thereby lowering the entropic barrier to the reaction.

The disclosure below describes in more detail how this complex is formed and provides results of experiments that show that the present invention can result in greatly improved reaction kinetics for $S_N2$-type reactions.

In addition to improved rate kinetics, the invention provides, in some embodiments, a diminishment of the traditional by-products associated with the nucleophilic substitution reaction. While not wishing to be bound by theory, it is theorized that the enhanced stability of the ether-stabilized sulfonate-metal ion leaving group favors the desired $S_N2$ reaction over other mechanisms (e.g. E1, E2, etc.) that are supported by various R groups.

The invention can be used to make a wide-variety of compounds having functional groups that introduced to the substrate as nucleophiles. For instance, ethanol can be converted into chloroethane, bromoethane, iodoethane, azoethane, acetonitrile, etc. Higher molecular weight compounds having hydroxyl groups can be easily converted into their corresponding halides, azides, cyanides, etc. Such compounds are ubiquitous in the art and have well-known properties as solvents, reagents for making target compounds (especially isotopically-enriched compounds), pharmaceuticals, diagnostic reagents, imaging agents, image contrast reagents, etc.

One particular compound that can be made by a method according to this invention is fluorodeoxyglucose $^{18}F$ (2-deoxy-2-(fluoro-$^{18}F$)-α-D-glucopyranose; $^{18}FDG$). The compound $^{18}FDG$ is a radioactive contrast reagent. It is listed in the Merck Manual, 12th Ed., under accession number 4162. Thus it has a well-known utility that would be accepted by one of skill in the art.

The compound $^{18}FDG$ can be prepared from readily available mannitol, which is first optionally selectively protected with one or more protecting groups PG) to prepare a reagent of the formula:

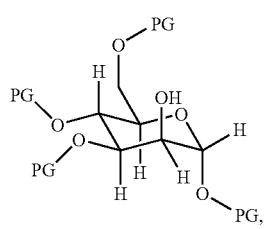

wherein each PG is H or optionally a protecting group. In one particular embodiment, the protecting groups are all acetyl groups.

The protected mannitol may then be reacted with a nucleophile assisting leaving group (NALG) precursor to form a NALG mannitol derivative. The NALG precursor may be attached to a polymer support so that, upon reaction with protected mannitol, the NALG mannitol derivative will become attached to polymer.

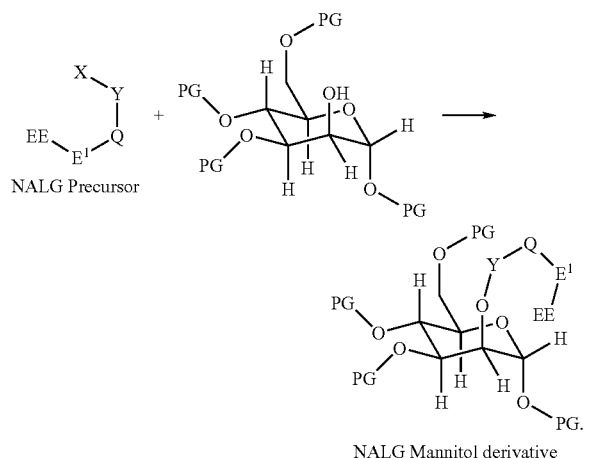

NALG Mannitol derivative

Reaction of the NALG mannitol derivative (an its polymer supported analog) with a suitable source of $^{18}F^-$, such as $Li^{18}F$, $Na^{18}F$, $K^{18}F$, etc., will displace the leaving group which it is believed is stabilized by the cation ($Li^+$, $Na^+$, $K^+$, etc.). The resulting product, hydroxyl-protected $^{18}FDG$, can then be deprotected and purified by known processes to give $^{18}FDG$.

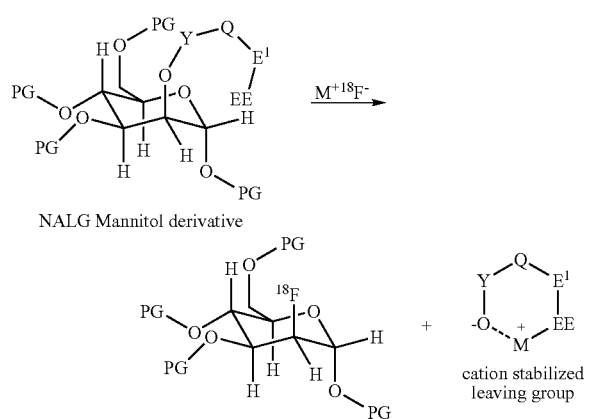

In accordance with aspects of this invention, it can be seen that the general methodology set forth herein can be used to prepare a wide variety of radioactive fluoride and iodide species, such as positron emission tomography (PET) reagents.

The invention can be further understood in the case of sulfonate-based leaving groups with reference to the following description and the appended claims. Variations for improved cation recognition in sulfonate-based nucleophile assisting leaving groups (NALGs) are described below. NALG 1 does not contain the aryl sulfonate group. NALG 2 is a more general formulation for the class of NALGs that have been studied and are provided by the present invention (specifically when X=CH, Z=$CO_2$, W=O, n=1, and the side-chain is ortho). NALG 3 contains a crown ether side-chain. In both 2 and 3, there are, in some embodiments, side-chains ortho to the sulfonate group.

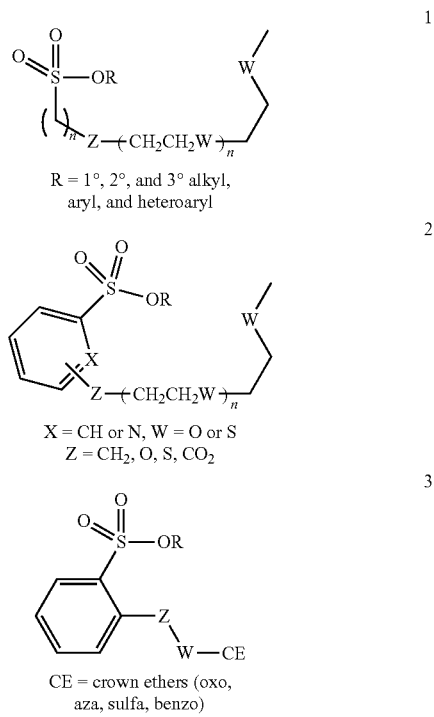

Overview of Some Embodiments of the Invention.

Many $S_N2$ reactions involving weak nucleophiles such as fluoride, chloride, azide, cyanide, and nitride are prohibitively slow and low-yielding. The inventors have developed an arylsulfonate-based NALG that greatly enhances the reaction rate by attracting the metal counter-cations of nucleophilic salts to the site of electrophilic attack. The NALG reported in this invention contains a diethylene glycol unit attached to a benzene sulfonyl group in the ortho orientation (Scheme 1). The concept can be described using lithium chloride (LiCl) as the nucleophilic salt, although other cations (e.g. mono- and di-valent metals) and nucleophiles (e.g. $F^-$, $Br^-$, $I^-$, $N_3^-$, nitride, $CN^-$, $R'O^-$ etc.) can be used. While not wishing to be bound by theory, upon addition of LiCl, it can be envisioned that the lithium cation will be coordinated by the three oxygen atoms of the diethylene glycol moiety. In solvents of low solvating ability, the chloride ion should remain ionically bonded to the diethylene glycol-coordinated lithium cation. Because of the ortho orientation of the diethylene glycol unit, the Li cation (and consequently the chloride nucleophile) is likely to be positioned near the site of electrophilic attack. In normal intermolecular $S_N2$ reactions, the nucleophile and electrophile must "find" each other, thus presenting a barrier (entropic) that slows down the reaction rate. The primary benefit of the NALG technology is that the nucleophilic portion of the salt (the chloride ion in this case) is localized near the site of attack (intramolecular) thereby reducing the entropic barrier and increasing the rate of product formation.

Scheme 1. Schematic explanation of the rate enhancement afforded by a NALG and other NALG designs according to the invention.

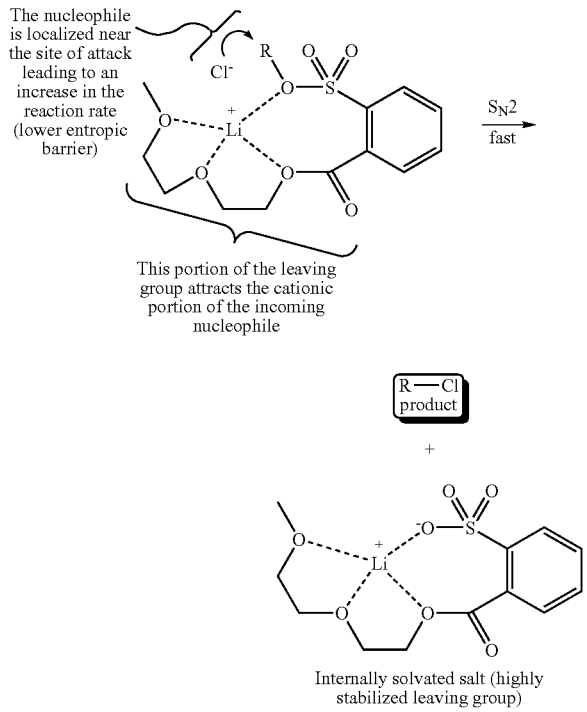

Reactions of the $S_N2$ type have often been described as more favorable when the leaving group is stabilized as it forms in the transition state. Using NALG technology, the leaving group resulting from an $S_N2$ reaction is likely to be more stable than traditional leaving groups. For example, the NALG resulting from the LiCl reaction (Scheme 1) is likely to form a highly stabilized (and entropically favored) internal ion pair where the sulfonate group ionically bonds to the lithium cation that is chelated by the nearby diethylene glycol moiety. While the supporting data for this invention involves a diethylene glycol-based NALG, the invention includes a variety of molecular designs to produce the acceleration effect as described in the previous section.

NALG technology can also be adapted to the solid-phase for use in combinatorial synthesis and other specialty applications by attaching NALGs of various designs to polymer supports. For example, the chlorination reaction described in Scheme 1 can be adapted to the solid-phase by linking the leaving group is linked to an insoluble polymer (Scheme 2). In this conception, the chloride has attacks the R group to give desired product as well as leaving group that is connected to an insoluble polymer. Due to its insolubility, this leaving group can be separated from the product (which is generally soluble in a reaction solvent) by a simple filtration step.

Scheme 2. Adaptation of NALG technology to solid-phase applications.

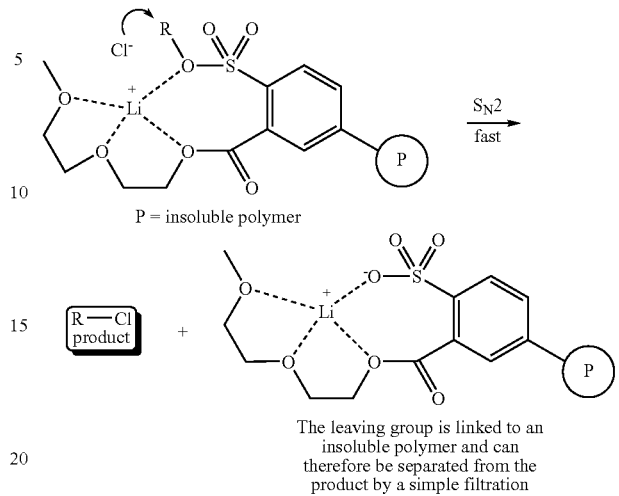

Finally, this invention also contemplates silicon-based alcohol protecting groups that are removed by the action of a metal fluoride salt for which the protecting group is highly selective. Silicone-based alcohol protecting groups are widely employed in organic synthesis and are usually removed by the action of a fluoride salt (e.g. tetrabutyl ammonium fluoride, LiF, etc.). An example of a fluoride assisting leaving group (FALG) containing a diethylene glycol unit is depicted in Scheme 3. While not wishing to be bound by theory, upon addition of LiF, it can be envisioned that the lithium cation will be coordinated by the three oxygen atoms of the diethylene glycol moiety. In solvents of low solvating ability, the fluoride ion should remain ionically bonded to the diethylene glycol-coordinated lithium cation. Because of the ortho orientation of the diethylene glycol unit, the Li cation (and consequently the fluoride nucleophile) is likely to be positioned near the site of electrophilic attack. In normal desilylation reactions, the fluoride and silicon electrophile must "find" each other, thus presenting a barrier (entropic) that slows down the reaction rate. The primary benefit of the FALG technology is that the fluoride portion of the salt is localized near the site of attack (intramolecular) thereby reducing the entropic barrier and increasing the rate of the desilylation reaction. The increased rate of desilylation of the FALG should allow for its selective removal in the presence of other silyl protected hydroxyl groups.

Scheme 3. Schematic explanation of the rate enhancement and salt selectivity afforded by a fluoride assisting leaving group (FALG) containing a diethylene glycol unit.

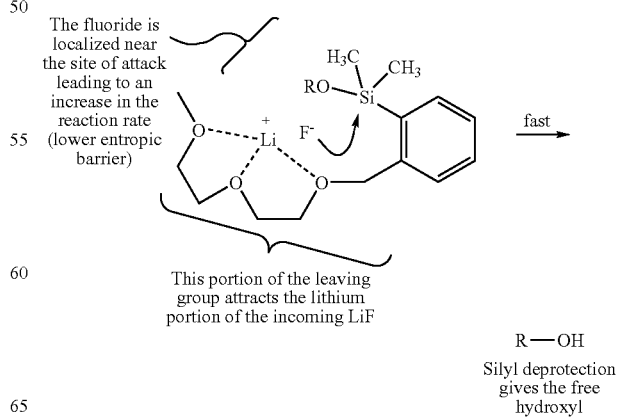

Experimental Results

The following experimental results involving arylsulfonate based nucleophile assisting leaving groups (NALGs) and comment thereon are presented to demonstrate the efficacy of the invention. These results are presented for illustrative purposes and there is no intent to limit the invention to the examples below.

Although reactions mediated by the classical $S_N2$ mechanism have proved overwhelmingly useful in synthesis, prohibitively slow reaction kinetics are often observed with sterically hindered secondary substrates and weak or poorly soluble nucleophiles. A number of strategies are routinely employed to expedite $S_N2$ reactions including the use of highly stabilized leaving groups (Zeliavi, J. Org. Chem., 40, 3870 (1975); Wu et al., J. Org. Chem., 39, 3014 (1974)) to increase the electrophilicity of the substrate and ionophilic phase transfer agents to transport poorly soluble nucleophilic salts into the solution phase. A variety of useful phase transfer agents have been developed such as quaternary ammonium salts, (Wang et al, J. Org. Chem., 55, 2344 (1990)), macrocyclic ethers, (Pedersen, J. Am. Chem. Soc., 89, 7017 (1967); Pedersen, et al., 11, 16 (1972); Stott, et al., J. Am. Chem. Soc., 102, 4810 (1980)) and podands (Kimura, et al. J. Org. Chem., 47, 2493 (1982); Kimura, et al., J. Org. Chem., 48, 195 (1983); Solov'ev, et al., J. Chem. Soc., Perkin Trans. 2., 1489 (1998). The invention provides embodiments in which electrophiles containing sulfonate leaving groups are rendered more reactive by modifying them to contain a cation chelating moiety that would attract nucleophilic metal salts to the site of attack. In this chelated form, the nucleophilic portion of the salt is localized near the electrophilic center, thus decreasing the entropic barrier relative to intermolecular reactions as depicted in equation 1.

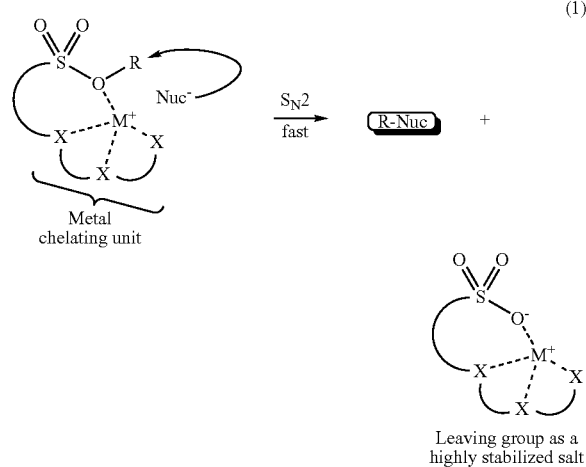

(1)

The invention further provides that chelated metal cation would stabilize the developing negative charge on the oxygens of the sulfonate leaving group in the transition state. (Gobbi, et al., J. Org. Chem. 60, 5954 (1995)). In addition, the invention provides for embodiments in which, by attaching an ion-selective moiety to the leaving group, the electrophilic substrate should be more reactive toward nucleophiles containing a specific metal countercation potentially leading to the development of salt-specific leaving groups. (Lippard, C & E News, August 7, p. 64 (2000)). The present invention provides for the synthesis and unique reactivity of an arylsulfonate-based nucleophile assisting leaving group (NALG) that contains a diethylene glycol unit attached to the aromatic ring in the ortho orientation, as well as a more general embodiment in which a diethylene glycol or crown ether is arranged in proximity to a sulfonate-based leaving group in an orientation that will allow the diethylene glycol or crown ether to form a chelate with the cation of a cation-nucleophile complex, thereby stabilizing the sulfonate leaving group.

In an embodiment of the invention, diethylene glycol-containing arylsulfonyl chloride 1 was prepared in 95% yield by treating sulfobenzoic acid anhydride with phosphorous pentachloride (Loev, et al., J. Org. Chem., 27, 1703 (1962)) followed by the addition of 2-methoxy ethoxy ethanol. Arylsulfonyl chloride 1 was then reacted with several alcohols to give the corresponding sulfonate esters 2 in yields ranging from 93-96% (see equation 2). Arylsulfonyl chloride 1 reacts with ethylene glycol leading to the exclusive formation of the mono-sulfonate product in 1 hour (89% yield) (Choudhary, et al., Tetrahedron, 56, 7291 (2000)).

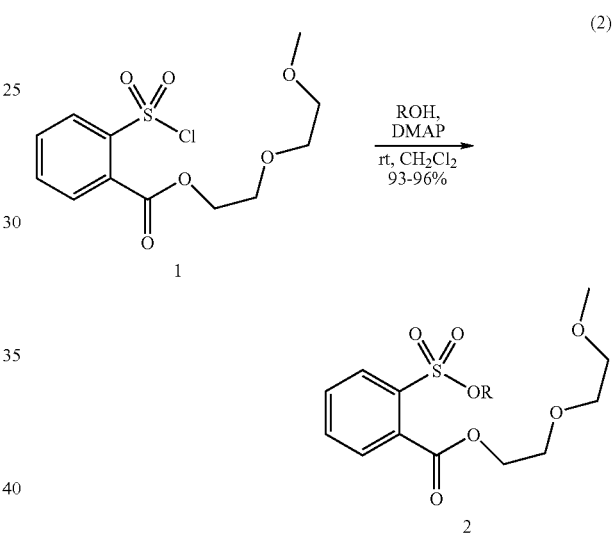

(2)

Sulfonate esters 2 (including primary) were exceptionally stable to silica gel chromatography even though (as discussed below) they were found to be significantly more reactive as $S_N2$ electrophiles than electronically equivalent sulfonate esters.

The rates of reaction of LiCl with glycol-containing sulfonate esters 2 were compared with their corresponding ortho-methylcarboxyphenyl sulfonates 3 and tosylates 4 (Table 1). In each case, substrates 2 reacted significantly faster than sulfonates 3. For example, the NALG derivative of 3-phenyl propanol (2a) reacted with LiCl to give 3-phenyl-propyl chloride in 0.5 h and in 98% yield which was over 8 times faster than the reaction with the electronically similar 3a (Table 1, entries 1 and 2). Comparing the rates of reaction of 3a with 4a (entry 3) seems to indicate that the ortho-positioned ester of 3a confers a 4 to 5 fold rate enhancement. Thus, it is an advantage of the invention that the diethylene glycol unit of 2a is responsible for the additional 8 fold chloride addition rate enhancement of 2a relative to 3a. Furthermore, when the diethylene glycol unit of 2a was replaced with a linear hydrocarbon chain as in 5a (the hydrocarbon equivalent of the diethylene glycol unit of 2a), the substrate behaved similar to methyl ester derivative 3a (compare entries 2 and 4). Methylcarboxyphenyl sulfonates of secondary alcohols analogous to 3a were prepared (3b and 3c), however, these substrates failed to give the corresponding alkyl chloride product when reacted with LiCl. Instead, numerous unidentified side products were observed. Thus the chlorination rates of diethylene glycol-containing NALG derivatives of 1-phenyl-2-propanol and 4-decanol (2b and 2c) were compared with their corresponding tosylates 4b and 4c (entries 5-8). In both cases a significant rate enhancement was observed. For example tosylate 4c gave only a 5% conversion to the alkyl chloride after 24 h while NALG 2c gave the chloride product in 96% yield after only 6 hours (compare entries 7 and 8).

sulfonyl ester of 3-phenyl propanol 2a reacted with LiBr in refluxing acetone to give 3-phenylpropylbromide in 97% yield in 0.1 h whereas the electronically equivalent methyl-carboxyphenyl sulfonate required 8 times longer (0.75 h) to give the same yield of product (entries 1 and 3 for LiBr). However, in regard to the reaction of both sodium and potassium bromide with substrates 2a and 3a, a remarkable reversal of selectivity was observed. The reaction of NaBr with 3a was complete (94% yield) in 3 h, whereas the reaction of NaBr with NALG 2a required over five times longer to achieve a similar yield (entries 1 and 3 for NaBr). This is the opposite of the trend observed in the reaction of these same two substrates

TABLE 1

Comparison of rates of lithium chloride addition to NALG sulfonate esters 2 versus sulfonates 3, 4, and 5.

| Entry | RO | X | Y | Substrate | Yield[a] (rxn time) |
|---|---|---|---|---|---|
| 1 | Ph~~~O | H | $CH_3O(CH_2CH_2O)_2CO$ | 2a | 98 (0.5 h) |
| 2 | Ph~~~O | H | $CH_3OCO$ | 3a | 94 (4 h) |
| 3 | Ph~~~O | $CH_3$ | H | 4a | 93 (18 h) |
| 4 | Ph-CH(CH₃)-O | H | $CH_3O(CH_2)_6OCO$ | 5a | 96 (6 h) |
| 5 | Ph-CH(CH₃)-O | H | $CH_3O(CH_2CH_2O)_2CO$ | 2b | 94 (8 h) |
| 6 | 4-decyl-O | $CH_3$ | H | 4b | 54 (22 h)[b] |
| 7 | 4-decyl-O | H | $CH_3O(CH_2CH_2O)_2CO$ | 2c | 96 (6 h) |
| 8 | 4-decyl-O | $CH_3$ | H | 4c | 5 (24 h)[b] |

[a] Isolated Yield
[b] Reaction was stopped and starting material recovered.

TABLE 2

Comparison of the rates of lithium, sodium, and potassium bromide additions to various alkyl sulfonates.

| | | % Isolated Yield (Reaction Time)[a] | | |
|---|---|---|---|---|
| Entry | Substrate | LiBr | NaBr | KBr |
| 1 | 2a | 97 (0.1 h) | 92 (16 h) | 50 (24 h) |
| 2 | 2a (DMF) | 95 (1.5 h) | 93 (3.5 h) | 94 (9 h) |
| 3 | 3a | 96 (0.75 h) | 94 (3 h) | 92 (15 h) |
| 4 | 4a | 83 (3 h) | 89 (28 h) | 38 (24 h) |
| 5 | 4a (DMF) | 93 (10 h) | 91 (7 h) | 94 (12 h) |
| 6 | 2b | 96 (2 h) | 11 (30 h)[c] | 0 (24 h)[c] |
| 7 | 4b | 81 (11 h) | 16 (30 h)[c] | 0 (24 h)[c] |
| 8 | 2c | 97 (1 h) | 23 (30 h)[c] | 0 (24 h)[c] |
| 9 | 4c | 95 (24 h)[b] | 33 (30 h)[c] | 0 (24 h)[c] |

[a] Except as noted, all reactions were performed in refluxing acetone. Reactions in DMF performed at room temp.
[b] Ratio of subsitution to elimination = 7.5:1
[c] Only product and unreacted substrate remained.

Similar trends were observed in reactions involving lithium bromides in refluxing acetone (Table 2). The NALG with LiBr. The reactions of NaBr and KBr with sulfonates derived from secondary alcohols also validate this trend (entries 6-9). These data seem to indicate that the diethylene glycol unit of 2a-c favors the chelation of the lithium cation but destabilizes $S_N2$ reactions involving sodium and potassium salts. Thus, in some embodiments of the invention, the cation $M^{x+}$ is preferably $Li^+$, whereas in other embodiments of the invention $M^{x+}$ may be other cations.

To further investigate the rate enhancement afforded by the diethylene-glycol NALG system, hindered 2-adamantanol was converted to the corresponding NALG-containing 6 (96% yield starting from 1). Upon treatment of NALG 6 with LiBr a conversion to the corresponding bromide in 98% yield in 16 h was observed. No side products involving rearrangement of the adamantane nucleus were observed. (Sinnott, et al., Chem. Commun., 1000 (1969)).[9] The corresponding adamantly tosylate gave no reaction even after 70 h in refluxing acetone. To our surprise, even the highly electrophilic 2-adamantyl triflate failed to give the bromide product when treated with LiBr in refluxing acetone for extended periods.

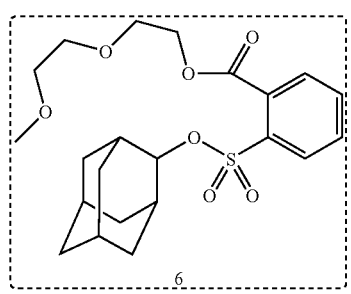

We reasoned that the discriminating ability of the flexible diethylene glycol coordinating arm of the various NALG substrates should decrease in polar or coordinating solvents. (Mizutani, et al., J. Org. Chem., 65, 6097 (2000); Maitra, Tetrahedron Lett., 39, 3255 (1998), Solov'ev, et al., J. Org. Chem., 61, 5221 (1996)). In the more polar DMF, the rate difference in the reaction between 2a and 4a with LiBr diminished to 5 times (compared to 30 times for acetone) whereas the corresponding NaBr and KBr reactions were only 2 times as fast with 2a than 4a indicating a decreased selectivity for the lithium salt (Table 2, entries 2 and 5). As anticipated, the use of 20% aqueous acetone as a solvent degraded the lithium selectivity of the bromination reaction of 2a from 30 fold in pure acetone to 5 fold in aqueous acetone (results not shown) (Adrian, et al., J. Am. Chem. Soc., 113, 678 (1991); Dishonig, et al., J. Org. Chem., 47, 147 (1982). A similar reduced selectivity for lithium was also observed in the reaction of 2a and 4a with lithium and sodium azide salts in 20% aqueous acetone.

Primary sulfonates 2a and 4a reacted with lithium, sodium and potassium p-ethylphenoxide in THF to give aryl ether product 7. A two-fold preference of NALG 2a for lithium p-ethylphenoxide relative to the sodium and potassium aryloxide salts (Table 3) was observed. It can be reasoned that the diminished NALG selectivity for the lithium salt was due to the coordinating capacity of THF. One of skill in the art will recognize that other polyether or crown ether side chains can be envisioned which would provide greater coordinating capacity in order to accommodate larger cations.

TABLE 3

Reaction of lithium, sodium and potassium p-ethyl-phenoxide with substrates 2a and 4a in THF to give product 7.

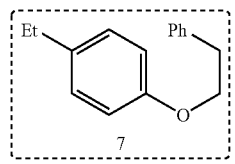

| Entry | Substrate | LiOAr | NaOAr | KOAr |
|---|---|---|---|---|
| 1 | 2a | 93 (8 h) | 93 (20 h) | 32 (24 h) |
| 2 | 4a | 92 (18 h) | 90 (22 h) | 26 (24 h) |

[a]Conditions: refluxing in THF

In conclusion, it has been demonstrated that a diethylene glycol-containing NALG can be used to significantly enhance $S_N2$-type reactions involving metal halides, azides, and aryloxides. The rate enhancement of the NALG-containing substrates is likely the result of the ability of the diethylene glycol unit to both attract the metal cation of the incoming nucleophile and to stabilize the newly-forming leaving group through internal chelation. The reactivity differences in the brominiation reactions involving lithium, sodium, and potassium bromide suggest that leaving groups can be designed to favor certain nucleophilic salts. The design of new NALGs possessing cation chelating units of greater specificity is currently underway.

Applications.

NALG technology will find a wide range of applications involving small-molecule organic synthesis.

Specialty Reagents—

Due to the rate enhancement and cation selectivity observed in experiments involving the NALG described in this disclosure, the invention will find application in both solution and solid-phase synthesis.

PET Labeling Agents—

Due to the rate enhancement of NALG technology, the invention contemplates the application of NALG technology to the synthesis of positron emitting labeling agents for use in PET medical imaging. Due to the short half-life of the radioisotopes used in PET such as $^{18}F$ ($t_{1/2}$=110 min) and $^{11}C$ ($t_{1/2}$=20 min), there is currently a great emphasis for the development of fast reactions involving these nuclei.

Experimental Methods

The following experimental methods were employed in the foregoing experiments.

General Considerations:

IR spectra were recorded as thin films on a Mattson Galaxy 4000 FT spectrophotometer. 1H, $^{13}C$ NMR spectra were recorded oil 400 and 100.75 MHz spectrometer respectively in $CDCl_3$. High-resolution mass spectra were obtained from the Mass Spectrometry Facility at the University of Florida, Gainesville. All the $^1H$ spectra are referenced internally to residual protio solvent signals or internal TMS standard. Data for $^1H$ NMR are recorded as follows: chemical shift (ppm), multiplicity (s, singlet: d, doublet; t, triplet; q, quartet; m, multiplet), integration, coupling constant (Hz). $^{13}C$ NMR spectra are reported in terms of chemical shift (δ, ppm). Reactions were monitored by TLC using silica gel 60 $F_{254}$ precoated 250 μm thick plates and visualized by UV light and stained with $KMnO_4$ spray. Column chromatography was performed using silica gel 60 (32-65 μm). Metal hydrides were stored in mineral oil (60% for NaH and 30% for KH) and were washed with hexane prior to use. The structures of the tosylate esters 4a-c (Table 1) were confirmed by comparison with their reported NMR spectra (4a (Suenaga, et al., Tetrahedron Lett., 44, 599 (2003), 4b (Zehavi et al., supra) and 4c (Magdelena et al., Z. Coll. Czech. Chem. Commun., 45, 3150 (1980)). 2-adamantyl tosylate (Suenaga et al., supra) and 2-adamantyl triflate (Suenaga et al., supra) were prepared according to the reported procedure.

The structure of the various alkyl chloride and bromide products were also confirmed by comparison with their reported NMR spectra (phenylpropylchloride, phenylpropylbromide, 1-phenyl-2-chloropropane, 4-chlorodecane, 4-bromodecane, 2-bromo adamantane.

Materials:

Reaction grade acetone, DMF, and dichloromethane were used without purification. THF was dried by filtration through an anhydrous alumina column. All reagents such as o-sulfobenzoic acid cyclic anhydride, phosphorous pentachloride, inorganic salts were used as purchased.

Procedure for the Preparation of Methoxyethoxyethyl 2-(Chlorosulfonyl) Benzoate (1)

A mixture of o-sulfobenzoic acid anhydride (9.0 g, 49 mmol) and phosphorous pentachloride (16.0 g, 74 mmol) was heated at 90° C. for 6 h. The oil was allowed to cool and dissolved in ether and rinsed with ice water to remove unreacted phosphorous pentachloride. The solvent was evaporated in vacuo leaving 10.2 g of oil. The crude oil (7.0 g, 29 mmol) was then dissolved in excess methoxyethoxyethanol (24.0 g, 200 mmol) and heat to 60° C. for 30 h. The reaction mixture was purified by flash chromatography by eluting with a hexane/acetone (85:15 v/v) to yield 1 as an oil (8.8 g, 95%): IR (neat) 1731 (C=O), 1353, 1196 ($SO_2$) cm$^{-1}$; $^1$HNMR (400 MHz, CDCl$_3$) δ 8.14 (dd, 1H, J=0.9 and 7.74 Hz), 7.80-7.69 (m, 2H), 4.57-4.54 (m, 2H), 3.86-3.84 (m, 2H), 3.67-3.65 (m, 2H), 3.55-3.53 (m, 2H), 3.36 (s, 3H); $^{13}$CNMR (100.75 MHz, CDCl$_3$) δ 166.0, 141.6, 135.4, 132.4, 131.6, 130.4, 129.2, 72.0, 70.6, 68.7, 65.9, 59.2; HRMS (EI) [M+H]$^+$: calcd for $C_{12}H_{16}ClO_6S$ 323.0356, found 323.0350.

Representative Procedure

Preparation of 3-phenylpropyl 2-(methoxyethoxyethylcarboxy)-1-benzosulfonate (2a)

To a dichloromethane solution (10 mL) of 1 (0.483 g, 1.5 mmol) was added DMAP (0.22 g, 1.8 mmol) under argon. The reaction mixture was cooled to 0° C. before the addition of phenylpropanol (0.275 g, 2.25 mmol). The resulting mixture was warmed to room temperature and stirred for 1 h. The solvent was evaporated in vacuo. The crude sulfonate ester was then purified by flash chromatography by eluting with hexane/acetone (70:30 v/v) to give 2a as a gummy material (0.6 g, 95%): IR (neat) 1733 (C=O), 1350, 1166 ($SO_2$) cm$^{-1}$; $^1$HNMR (400 MHz, CDCl$_3$) δ 7.98 (d, J=7.3 Hz, 1H), 7.70-7.68 (m, 2H), 7.63-7.58 (m, 1H), 7.24-7.07 (m, 5H), 4.54-4.52 (m, 2H), 4.16 (t, J=6.2 Hz, 2H), 3.84-3.82 (m, 2H), 3.66-3.63 (m, 2H), 3.53-3.51 (m, 2H), 3.55 (s, 3H), 2.69 (t, J=7.3 Hz), 1.97-2.04 (m, 2H); $^{13}$C NMR (100.75 MHz, CDCl$_3$) δ 167.0, 140.6, 134.1, 133, 7, 133, 5, 131.0, 129.9, 129.8, 128.6, 128.6, 126.3, 72.0, 70.8, 70.6, 68.9, 65.5, 59.2, 31.5, 30.7; HRMS (EI) [M+H]$^+$: calcd for $C_{21}H_{27}O_7S$ 423.1477, found 423.1469.

1-phenyl-2-propyl 2-(methoxyethoxyethylcarboxy)-1-benzosulfonate (2b)

(0.62 g, 93%): IR (neat) 1734 (C=O), 1355, 1176 ($SO_2$) cm$^{-1}$; $^1$H NMR (400 MHz, CDCl$_3$ δ7.78 (d, J=7.9 Hz, 1H), 7.60-7.59 (m, 2H), 7.50-7.45 (m, 1H), 7.19-7.07 (m, 5H), 4.94 (qdd, J=6.3, 6.3, 6.7 Hz, 1H), 4.53-4.51 (m, 2H), 3.84-3.81 (m, 2H), 3.67-3.64 (m, 2H), 3.55-3.52 (m, 2H), 3.61 (s, 3H), 3.00 (dd, J=6.3, 13.7 Hz, 1H), 2.82 (dd, J=6.8, 13.7, 1H), 1.32 (d, J=6.2 Hz, 3H); $^{13}$CNMR (100.75 MHz, CDCl$_3$) δ 167.1, 136.3, 135.1, 133.3, 131.1, 130.9, 129.7, 129.5, 129.4, 128.6, 126.9, 82.2, 72.0, 70.65, 68.9, 65.5, 59.2, 43.0, 20.7; HRMS (EI) [M+H]$^+$; calcd for $C_{21}H_{27}O_7S$ 422.1477, found 423.1485.

4-decyl 2-(methoxyethoxyethylcarboxy)-1-benzosulfonate (2c)

(0.61 g, 96%): IR (neat) 1732 (C=O), 1365, 1156 ($SO_2$) cm$^{-1}$; $^1$HNMR (400 MHz, CDCl$_3$) δ 8.00 (d, J=7.5 Hz, 1H), 7.67-7.58 (m, 3H), 4.72 (tt, J=6.1, 6.0 Hz, 1H), 4.53-4.50 (na, 2H), 3.84-3.81 (m, 2H), 3.67-3.65 (il, 2H), 3.55-3.53 (m, 2H), 3.36 (s, 3H), 1.65-1.5 (m, 5H), 1.36-1.09 (m, 9H), 0.84 (t, J=6.6 Hz, 3H), 0.82 (t, J=7.4, 3H); $^{13}$CNMR (100.75 MHz, CDCl$_3$) δ 167.1, 135.7, 133.3, 130.7, 129.6, 129.4, 86.0, 72.0, 70.6, 68.9, 65.4, 59.2, 36.4, 34.3, 31.7, 29.1, 22.1, 18.1, 14.2, 14.0; HRMS (EI) [M+H]$^+$: calcd for $C_{22}H_{37}O_7S$ 445.2260, found (M+H)$^+$ 445.2263.

Synthesis of 2-hydroxyethyl 2-(methoxyethoxyethylcarboxy)-1-benzosulfonate (2d)

To a dichloromethane solution (10 mL) of 1 (0.45 g, 1.4 mmol) was added DMAP (0.24 g, 1.68 mmol) under argon. The reaction mixture was cooled down to 0° C. prior to the addition of ethylene glycol (0.16 g, 2.5 mmol). The resulting mixture was warmed to room temperature and stirred for 45 min. The solvent was evaporated in vacuo to give a gummy crude material which was purified by flash chromatography by elution with hexane/acetone (40:60 v/v) to give 2e (0.43 g, 89%): IR (neat) 3454 (OH), 1739 (C=O), 1353, 1165 ($SO_2$) cm$^{-1}$; $^1$HNMR (400 MHz, CDCl$_3$) δ 8.07 (d, J=7.4 Hz, 1H), 7.62-7.49 (m, 3H), 4.55-4.53 (m, 2H), 4.27-4.20 (m, 2H), 3.87-3.86 (m, 2H), 3.76-3.72 (m, 2H), 3.68-3.66 (m, 2H), 3.56-3.54 (m, 2H), 3.48 (t, J=6.8 Hz, 1H), 3.36 (s, 3H); $^{13}$CNMR (100.75 MHz, CDCl$_3$) δ 167.3, 134.1, 133.4, 133.2, 131.1, 130.7, 130.4, 72.9, 71.9, 70.47, 69.0, 65.5, 60.3, 59.2; HRMS (EI) [M+H]$^+$: calcd. for $C_{14}H_{21}O_8S$ 349.0957, found 349.0947.

Synthesis of 3-phenylpropyl 2-(heptylcarboxy)-1-benzosulfonate (5a)

A mixture of o-sulfobenzoic acid anhydride (1.83 g, 10 mmol) and phosphorous pentachloride (3.12 g, 15.0 mmol) was heated at 90° C. for 6 h. The oil was dissolved in ether and rinsed with ice water to remove unreacted phosphorous pentachloride. The solvent was evaporated in vacuo leaving 2.2 g of an oil. The crude oil was then dissolved in 1-heptanol and heated to 60° C. for 30 h. The reaction mixture was purified by flash chromatography by eluting with a hexane/acetone (85:15 v/v) to yield n-heptyl 2-(chlorosulfonyl)benzoate as an oil. Yield: 0.5 g, 21%. IR (neat): 1732 (C=O), 1357, 1196 ($SO_2$) cm$^{-1}$; $^1$H NMR (400 MHz, CDCl$_3$) δ 8.15 (brdd, J=1.2 and 8.2 Hz, 1H), 7.80-7.76 (m, 1H), 7.72-7.67 (m, 2H), 4.36 (t, J=6.9, 2H), 1.81-1.73 (m, 2H), 1.41-1.25 (m, 8H), 0.85 (t, 3H, J=6.9 Hz); $^{13}$C NMR (400 MHz, CDCl$_3$) δ 166.2, 135.3, 131.5, 130.2, 129.2; HRMS (EI) [M+H]$^+$; calcd. for $C_{14}H_{20}ClO_4S$ 319.0771, found 319.0782.

To a dichloromethane solution (10 mL) of heptyl 2-(chlorosulfonyl)benzoate (0.4 g, 1.25 mmol) was added DMAP (0.18 g, 1.5 mmol) under argon. The reaction mixture was cooled to 0° C. before the addition of plenylpropanol (0.34 g, 2.25 mmol). The resulting mixture was warmed to room temperature and stirred for 1 h. The solvent was evaporated in vacuo. The crude sulfonate ester was then purified by flash chromatography by eluting with hexane/acetone (70:30 v/v) to give 5a as a gummy material. (0.45 g, 84%). IR (neat) 1733 (C=O), 1355, 1165 ($SO_2$) cm$^{-1}$; $^1$HNMR (400 MHz, CDCl$_3$) δ 7.99 (d, J=8.3 Hz, 1H), (7.71-7.58 (m, 3H), 7.25-7.14 (m, 3H), 7.09-7.07 (m, 2H), 4.36 (t, 2H, J=6.9 Hz, 2H), 4.16 (t, J=6.2 Hz, 2H), 2.7 (t, J=7.3 Hz, 2H), 1.97-2.04 (m, 2H), 1.77 (tt, J=6.8 and 7.0 Hz), 1.21-1.44 (m, 8H), 0.87 (t, J=6.9, 3H); $^{13}$CNMR (100.75 MHz, CDCl$_3$) δ 167.1, 140.5, 134.1, 133.9, 133.7, 130.8, 129.9, 129.6, 128.7, 128.6, 126.3, 70.7, 67.0, 31.9, 31.6, 30.7, 29.1, 28.6, 26.0, 22.8, 14.3; HRMS (EI) [M+H]+: calcd for $C_{23}H_{31}O_5S$ 419.1892, found 419.1907.

Synthesis of 2-adamantyl 2-(methoxyethoxyethylcarboxy)-1-benzosulfonate (6)

To a pyridine solution (10 mL) of 1 (900 mg, 2.8 mmol) was added 2-adamantanol (850 mg, 5.5 mmol) at 0° C. The reaction mixture was slowly warmed to room temperature and allowed to stir for 16 h. The pyridine was removed in vacuo resulting in a gummy material. The crude material was purified by flash chromatography by elution with a hexane/acetone (70:30 v/v) to give 6 (1.18 g, 96%) as a gummy material. IR (neat) 1734 (C=O), 1360, 1185 ($SO_2$) cm$^{-1}$; $^1$H NMR (400 MHz, CDCl$_3$) δ 8.02 (d, J=7.4 Hz, 1H), 7.67-7.58 (m, 3H), 4.83 (m, 1H), 4.54-4.51 (m, 2H, 3.67-3.65 (m, 2H), 3.55-3.53 (m, 2H), 3.36 (s, 3H), 2.10-2.03 (m, 4H), 1.83-180 (m, 4H), 1.69-1.62 (m, 4H), 1.53-1.50 (m, 2H); $^{13}$C NMR (100.75 MHz, CDCl$_3$) δ 167.0 (CO), 135.34, 133.1, 130.8, 129.7, 129.4, 87.8, 72.0, 70.6, 68.9, 65.4, 59.2, 37.3, 36.5, 32.9, 31.3, 27.0, 24.7; HRMS (EI) [(M+2H)—$C_{10}H_{15}$]+: calcd for $C_{12}H_{17}O_7S$ 305.0695, found 305.0699.

Representative Procedure

Preparation of 3-phenylpropyl 2-(methylcarboxy)-1-benzosulfonate (3a)

To a dichloromethane solution (10 mL) of methyl 2-(chlorosulfonyl)benzoate (0.35 g, 1.5 mmol) was added DMAP (0.21 g, 1.8 mmol) under argon. The reaction mixture was cooled to 0° C. before the addition of phenyl propanol (0.0.5 g, 3.75 mmol). The resulting mixture was warmed to room temperature and stirred for 1-14 h. The solvent was evaporated in vacuo. The sulfonate ester, 3a was purified by flash chromatography. Elution with a hexane/acetone (85:15 v/v) mixture yielded a gummy material in 41% (0.4 g) yield. IR (neat): 1737 (CO), 1355, 1170 ($SO_2$) cm$^{-1}$; $^1$HNMR (400 MHz, CDCl$_3$) δ 8.00 (dd, J=1.0 and 7.7 Hz). 7.72-7.59 (i1, 3H), 7.26-7.15 (m, 3H), 7.10-1.08 (m, 2H), 4.16 (t, J=6.2 Hz, 2H), 2.69 (t, J=7.34 Hz, 2H), 2.05-1.98 (m, 2H), 3.96 (s, 31H); $^{13}$CNMR (100.75 MHz, CDCl$_3$) δ 167.5, 140.5, 134.32, 133.7, 133.5, 131.0, 130.0, 129.6, 128.7, 128.6, 126.3, 70.7, 53.54, 31.62, 30.75; HRMS (EI) [M+H]+: calcd for $C_{17}H_{19}O_5S$ 335.0975, found 335.0940.

(1-phenyl-2-propyl 2-(methylcarboxy)-1-benzosulfonate) (3b)

(0.49 g, 74%). IR (neat): 1736 (CO), 1355, 1185 ($SO_2$) cm$^{-1}$; $^1$H NMR (400 MHz, CDCl$_3$) δ 7.80 (dd, J=1 and 7.9 Hz, 1H), 7.63-7.50 (m, 2H), 7.51-7.46 (m, 1H), 7.21-7.15 (m, 3H), 7.10-7.08 (m, 2H), 4.97 (qdd, J=6.3, 6.3, 6.7 Hz), 3.95 (s, 3H), 3.01 (dd, J=6.3 and 13.7 Hz, 1H), 2.83 (dd, J=6.8 and 13.7 Hz, 1H), 1.34 (d, J=6.2 Hz, 3H); $^{13}$C NMR (100.75 MHz, CDCl$_3$) δ 167.6, 136.3, 135.2, 133.3, 133.2, 130.9, 129.7, 129.5, 129.2, 128.6, 127.0, 82.1, 53.4, 43.0, 20.6; HRMS (EI) [M+H]+: calcd for $C_{17}H_{19}O_5S$ 335.0953, found 335.0945.

(4-decyl 2-(methylcarboxy)-1-benzosulfonate), (3c)

(0.24 g, 68%). IR (thin film): 1736 (CO), 1357, 1167 ($SO_2$) cm$^{-1}$; $^1$H NMR (400 MHz, CDCl$_3$) δ 8.01 (dd, J=1.2 and 7.6 Hz), 7.68-7.68 (M, 3H), 4.37 (tt, J=6.0 and 6.1 Hz, 1H), 3.94 (s, 3H), 1.67-1.51 (m, 5H), 1.34-1.15 (m, 10H), 0.84 (t, J=6.8 Hz, 3H), 0.83 (t, J=7.3 Hz, 3H); $^{13}$C NMR (100.75 MHz, CDCl$_3$) δ 167.6, 135.8, 133.3, 131.6, 130.7, 129.6, 129.28, 85.9, 53.4, 36.4, 34.2, 31.79, 29.1, 24.7, 22.7, 18.1, 14.2, 14.0; HRMS (EI) [M+H]+: calcd for $C_{18}H_{29}O_5S$ 357.1736, found 357.1739.

Representative procedure—Reaction of NALG sulfonate 2a with NaBr.

Acetone as Solvent:

Aryl sulfonate ester, 2a (0.05 g, 0.11 mmol) was dissolved in acetone, NaBr (0.04 g, 0.4 mmol) was added to it. The reaction mixture was stirred at room temperature/reflux conditions. The reactions were monitored carefully by TLC till the disappearance of starting material. Solvent was evaporated in vacuo. The reaction mixtures were washed with water to remove excess inorganic salts and extracted in EtOAc and dried over sodium sulfate. The organic layer was evaporated giving pure desired products. Yields and reaction times are given in (Table 1 and 2).

DMF as solvent: Aryl sulfonate ester, 2a (0.05 g, 0.0.11 mmol) was dissolved in DMF, NaBr (0.04 g, 0.4 mmol) was added to it. The reaction mixture was stirred at room temperature. The reactions were monitored carefully by TLC till the disappearance of starting material. Solvent was evaporated in vacuo. The reaction mixtures were washed with water to remove excess inorganic salts and extracted in ether and dried over sodium sulfate. The organic layer was evaporated giving pure desired products. Yields and reaction times are given in (Table 2).

Representative Procedure

Synthesis of 3-phenylpropyl 4-ethyl phenyl ether (7)

To a suspension of LiH (0.005 g, 0.6 mmol) in THF was added p-ethyl phenol (0.08 g, 0.68 mmol) very slowly at 0° C. After 30 min of stirring at room temperature, the sulfonate ester, 2a (0.075 g, 0.17 mmol) was added to it and the reaction mixture was heated at 65° C. for 8 h. The reaction mixture was washed very carefully with cold water and extracted in EtOAc and dried over sodium sulfate. The organic layer was evaporated and the crude gummy material was purified by flash chromatography giving 0.038 g (93%) of an oil. $^1$H NMR (400 MHz, CDCl$_3$) δ 7.31-7.18 (m, 5H), 7.13-7.09 (m, 2H), 6.85-6.81 (m, 2H), 3.94 (t, J=6.2 Hz, 2H), 2.84 (t, J=7.6 Hz, 2H), 2.58 (q, J=7.5, 2H), 2.13-2.03 (m, 2H), 1.21 (t, J=7.5 Hz, 3H); $^{13}$CNMR (100.75 MHz, CDCl$_3$) 141.8, 130.6, 128.9, 128.7, 128.6, 126.1, 114.6, 67.1, 32.4, 31.1, 28.2, 16.1; HRMS (EI) [M]+: calcd for $C_{17}H_{20}O$ 240.1514, found 240.1510.

What is claimed is:

1. A compound having the formula:

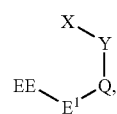

wherein:
EE is a crown ether;
$E^1$ is a linking group selected from $CH_2$, S, CO

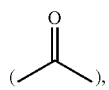, and $CO_2$

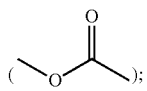;

Q is an optionally partially unsaturated cycloalkyl or aryl, each of which may be further substituted;
Y is $SO_2$ or $SiR^6R^7$,
wherein each of $R^6$ and $R^7$ is independently an optionally substituted alkyl group or together with the Si form a silane ring; and
X is a leaving group.

2. The compound of claim 1
wherein:
Y is $SO_2$; and
$E^1$ is attached ortho to Y on Q.

3. The compound of claim 2, having the structure:

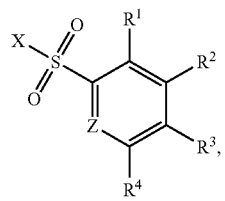

wherein:
Z is C linked to $E^1$;
X is chloride, bromide or fluoride; and
$R^1$-$R^4$ is independently $CH_3$ or H.

4. The compound of claim 1,
wherein:
Y is $SiR^6R^7$ wherein each of $R^6$ and $R^7$ is independently an optionally substituted alkyl group or together with the Si form a silane ring; and
X is selected from the group consisting of fluoride, chloride, and bromide.

5. A compound having the formula:

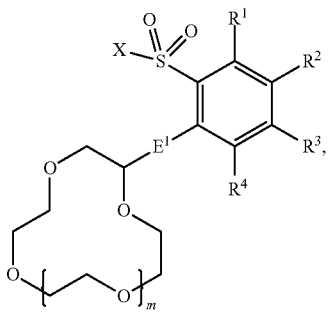

wherein
m is an integer of 1 to 3;
$E^1$ is $CH_2$, CO or $CO_2$;

each of $R^1$-$R^4$ is independently selected from the group consisting of H and $CH_3$, or two adjacent members of the group $R^1$-$R^4$ combine with the benzene ring to which they are attached to form a fused cyclo ring structure and the remaining two members of the group of $R^1$-$R^4$ are H or $CH_3$; and
X is a leaving group.

6. A compound having the formula:

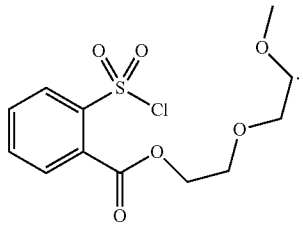 [SMILES: COCCOCCOC(=O)c1ccccc1S(=O)(=O)Cl]

7. A process of using a compound having the formula:

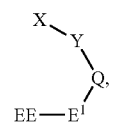

wherein:
EE is a crown ether;
$E^1$ is a linking group selected from $CH_2$, S, CO

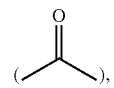, and $CO_2$

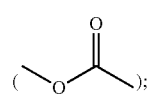;

Q is an optionally partially unsaturated cycloalkyl or aryl, each of which may be further substituted;
Y is $SO_2$ or $SiR^6R^7$,
wherein each of $R^6$ and $R^7$ is independently an optionally substituted alkyl group or together with the Si form a silane ring;
X is a leaving group;
comprising reacting said compound with an alcohol of the formula R—OH to replace X with OR
where R is an optionally substituted alkyl group, an optionally substituted alkenyl group, an optionally substituted alkynyl group or an optionally substituted cyclic group.

8. The process of claim 7:
wherein:
CO or $CO_2$;
Y is $SO_2$; and
X is a leaving group; wherein the Y and the $E^1$ groups are positioned adjacent to one another on the Q.

9. The process of claim 7
wherein; and
X is a leaving group selected from chloride, bromide and fluoride.

10. The process of claim 7 wherein the compound has the structure:

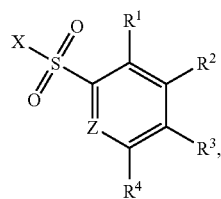

Z is C linked to $E^1$; and
$R^1$-$R^4$ is independently selected from the group consisting of H and $CH_3$, or two adjacent members of the group $R^1$-$R^4$ combine with the benzene ring to which they are attached to form a fused cyclo ring structure and the remaining two members of the group of $R^1$-$R^4$ are H or $CH_3$.

11. The process of claim 10 wherein X is sulphonate.

12. A process of using a compound, having the formula:

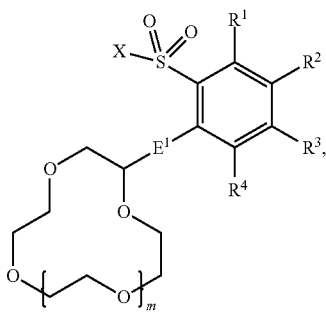

wherein
m is an integer of 1 to 3;
each of $R^1$-$R^4$ is independently selected from the group consisting of H and $CH_3$, or two adjacent members of the group $R^1$-$R^4$ combine with the benzene ring to which they are attached to form a fused cyclo ring structure and the remaining two members of the group of $R^1$-$R^4$ are H or $CH_3$;
comprising reacting said compound with an alcohol of the formula R—OH to replace $SO_2X$ with the OR;
where R is an optionally substituted alkyl group, an optionally substituted alkenyl group, an optionally substituted alkynyl group or an optionally substituted cyclic group.

13. A process of using a compound having the formula:

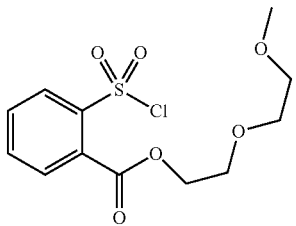 [SMILES: COCCOCCOC(=O)c1ccccc1S(=O)(=O)Cl]

comprising reacting said compound with an alcohol of the formula ROH wherein $SO_2Cl$ is replaced with OR where R is an optionally substituted alkyl group, an optionally substituted alkenyl group, an optionally substituted alkynyl group or an optionally substituted cyclic group.

* * * * *

UNITED STATES PATENT AND TRADEMARK OFFICE
CERTIFICATE OF CORRECTION

PATENT NO. : 8,822,707 B2
APPLICATION NO. : 11/667414
DATED : September 2, 2014
INVENTOR(S) : Salvatore Lepore It is certified that error appears in the above-identified patent and that said Letters Patent is hereby corrected as shown below:

On the Title Page,

Item (57), Abstract
Line 7, "toxyl group" should read --tosyl group--.

In the Specification,

Column 2,
Line 28, "filtration" should read --filtration.--.

Column 3,
Line 24, "allyl group" should read --alkyl group--.
Line 63, "allyl group" should read --alkyl group--.

Column 4,
Line 20, "$M_{x+}$ with" should read --$M^{x+}$ with--.
Line 54, "groups PG)" should read --groups (PG)--.

Column 5,
Line 32, "(an its polymer" should read --(and its polymer--.

Column 7,
Line 62, "chloride has attacks" should read --chloride attacks--.

Column 9,
Line 16, "(Zeliavi" should read --(Zehavi--.

Signed and Sealed this
Seventeenth Day of March, 2015

Michelle K. Lee
*Director of the United States Patent and Trademark Office*

Column 11,
Line 31, "CH₃O(CH₂)₆OCO" should read --CH$_3$(CH$_2$)$_6$OCO--.

Column 13,
Line 29, "Dishonig" should read --Dishong--.

Column 14,
Line 33, "1H, $^{13}$C" should read --$^1$H, $^{13}$C--.
Line 34, "oil 400" should read --on 400--.

Column 15,
Line 41, "133,7, 133, 5" should read --133.7, 133.5--.

Column 16,
Lines 1-2, "4.53-4.50 (na, 2H)" should read --4.53-4.50 (m, 2H)--.
Line 2, "3.67-3.65 (il, 2H)" should read --3.67-3.65 (m, 2H)--.

Column 17,
Line 17, "(m, 2H, 3.67-3.65" should read --(m, 2H), 3.67-3.65--.
Lines 33-34, "(0.0.5 g" should read --(0.5 g--.
Lines 40-41, "7.72-7.59 (il, 3H)" should read --7.72-7.59 (m, 3H)--.
Lines 42-43, "(s, 31H)" should read --(s, 3H)--.
Line 66, "(M, 3H)" should read --(m, 3H)--.

In the Claims,

Column 20,
Lines 64-67,
"9. The process of claim 7
wherein; and
X is a leaving group selected from chloride, bromide and fluoride."
should read
--9. The process of claim 7 wherein X is selected from chloride, bromide and fluoride.--.